(12) United States Patent
Bayer et al.

(10) Patent No.: US 10,149,947 B2
(45) Date of Patent: Dec. 11, 2018

(54) AUTOMATIC DRUG INJECTION DEVICE WITH SOPHISTICATED DRIVE MECHANISM

(71) Applicant: SANOFI, Paris (FR)

(72) Inventors: Stefan Bayer, Wurselen (DE); Daniel Berning, Baesweiler (DE); Philippe Blank, Dusseldorf (DE); Wolfgang Pelzer, Kreuzau (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 261 days.

(21) Appl. No.: 14/782,705

(22) PCT Filed: Apr. 8, 2014

(86) PCT No.: PCT/EP2014/056978
§ 371 (c)(1),
(2) Date: Oct. 6, 2015

(87) PCT Pub. No.: WO2014/166900
PCT Pub. Date: Oct. 16, 2014

(65) Prior Publication Data
US 2016/0067417 A1    Mar. 10, 2016

(30) Foreign Application Priority Data
Apr. 10, 2013   (EP) .................................... 13163078

(51) Int. Cl.
*A61M 5/315*   (2006.01)
*A61M 5/20*    (2006.01)
*A61M 5/31*    (2006.01)

(52) U.S. Cl.
CPC ...... *A61M 5/31548* (2013.01); *A61M 5/2033* (2013.01); *A61M 5/3158* (2013.01);
(Continued)

(58) Field of Classification Search
CPC ............ A61M 5/3155; A61M 5/31551; A61M 5/31563; A61M 5/31583; A61M 5/31585;
(Continued)

(56) References Cited

U.S. PATENT DOCUMENTS

| 6,796,970 B1* | 9/2004 | Klitmose | .............. A61M 5/315 604/207 |
| 2006/0069355 A1 | 3/2006 | Judson et al. | |

(Continued)

FOREIGN PATENT DOCUMENTS

| GB | 143 084 | 5/1920 |
| JP | 2009-529396 | 8/2009 |

(Continued)

OTHER PUBLICATIONS

International Preliminary Report on Patentability in International Application No. PCT/EP2014/056978, dated Oct. 13, 2015, 10 pages.

(Continued)

*Primary Examiner* — Kami A Bosworth
*Assistant Examiner* — William Carpenter
(74) *Attorney, Agent, or Firm* — Fish & Richardson P.C.

(57) ABSTRACT

A drug delivery device for setting and dispensing of a dose of a medicament includes a housing extending in an axial direction and a piston rod to operably engage with a piston of a cartridge to displace the piston in a distal axial direction. The drug delivery device further includes a drive spindle operably engageable with the piston rod during dose dispensing and a drive member axially displaceable relative to the drive spindle against the action of a spring element during dose setting and being threadedly engaged with the drive spindle to form a spindle gear.

20 Claims, 16 Drawing Sheets

(52) U.S. Cl.
CPC .... *A61M 5/31553* (2013.01); *A61M 5/31583* (2013.01); *A61M 5/31585* (2013.01); *A61M 5/31591* (2013.01); *A61M 5/31593* (2013.01); *A61M 5/3157* (2013.01); *A61M 5/31541* (2013.01); *A61M 5/31558* (2013.01); *A61M 5/31563* (2013.01); *A61M 5/31575* (2013.01); *A61M 2005/202* (2013.01); *A61M 2005/2086* (2013.01); *A61M 2005/314* (2013.01); *A61M 2005/3126* (2013.01); *A61M 2005/3143* (2013.01); *A61M 2005/3152* (2013.01); *A61M 2005/3154* (2013.01); *A61M 2005/31508* (2013.01); *A61M 2205/581* (2013.01)

(58) Field of Classification Search
CPC .......... A61M 5/31586; A61M 5/31548; A61M 2005/3152; A61M 5/31558
See application file for complete search history.

(56) References Cited

U.S. PATENT DOCUMENTS

| | | | |
|---|---|---|---|
| 2007/0244445 A1* | 10/2007 | Moller | A61M 5/24 604/207 |
| 2009/0048561 A1 | 2/2009 | Burren et al. | |
| 2009/0062748 A1* | 3/2009 | Moller | A61M 5/31511 604/211 |
| 2010/0152671 A1* | 6/2010 | Raab | A61M 5/31555 604/207 |
| 2013/0231613 A1* | 9/2013 | Leak | A61M 5/19 604/191 |

FOREIGN PATENT DOCUMENTS

| | | |
|---|---|---|
| JP | 2013-506447 | 2/2013 |
| WO | WO 2001/087386 | 11/2001 |
| WO | WO 2002/076535 | 10/2002 |
| WO | WO 2007/104697 | 9/2007 |
| WO | WO 2008/053243 | 5/2008 |
| WO | WO 2010/149717 | 12/2010 |
| WO | WO 2011/039208 | 4/2011 |
| WO | WO 2012/038721 | 3/2012 |
| WO | WO 2012/072554 | 6/2012 |

OTHER PUBLICATIONS

International Search Report and Written Opinion in International Application No. PCT/EP2014/056978, dated May 15, 2014, 14 pages.
Rote Liste, "50. Hypophysen-, Hypothalamushormone, andere regulatorische Peptide u. ihre Hemmstoffe," Chapter 50, ed. 2008, 20 pages.

* cited by examiner

A-A

B-B

B-B ions of typical drug delivery devices the size of such dose indicating numbers is fairly small. For visually impaired persons correct reading of comparatively tiny numbers may therefore be rather difficult. However, since such drug delivery devices are intended for self-medication treatment, it is of importance, that the user is able to correctly determine the size of dose actually set.

AUTOMATIC DRUG INJECTION DEVICE WITH SOPHISTICATED DRIVE MECHANISM

CROSS-REFERENCE TO RELATED APPLICATIONS

This application is a § 371 U.S. National Stage Application of PCT/EP2014/056978, filed Apr. 8, 2014, which claims priority to European Patent Application 13163078.2, filed Apr. 10, 2013, the entire contents of which are incorporated herein by reference.

The present invention relates to a drive mechanism for a drug delivery device and to a respective drug delivery device. In particular, the invention relates to an injection device such like a pen-type injector inter alia comprising a single and/or a last-dose limiting mechanism and further comprising a comparatively large dose indicating display.

BACKGROUND AND PRIOR ART

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, which is adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a set dose is entirely injected. There already exist some drug delivery devices with end-of-content mechanisms or last dose mechanisms.

Drug delivery devices such like pen type injectors also provide a dose indicating mechanism which is operable to display the size of a set dose to a user. Typically, the housing of such drug delivery devices comprises a dose indicating window in which a number representing the size of the dose shows up.

Especially with elderly patients or users suffering impaired vision, reading of such dose indicating numbers is sometimes difficult. With devices adapted for injection of e.g. insulin, typical dose sizes may vary between 0 and 120 I.U. (International Units) of insulin. Due to the rather compact design and limited geometrical dimensions of typical drug delivery devices the size of such dose indicating numbers is fairly small. For visually impaired persons correct reading of comparatively tiny numbers may therefore be rather difficult. However, since such drug delivery devices are intended for self-medication treatment, it is of importance, that the user is able to correctly determine the size of dose actually set.

OBJECTS OF THE INVENTION

It is therefore an object of the present invention to avoid disadvantages of known drug delivery devices and to provide a drive mechanism of a drug delivery device allowing for an intuitive operation, both for setting and for dispensing of a dose. It is another object to provide a dose indicating mechanism which is easy and unequivocal to read even for persons suffering impaired vision.

In another object, the invention serves to provide a drive mechanism of a drug delivery device for setting and dispensing of a dose of a medicament and further featuring a single and/or a last dose limiting mechanism.

It is a further aim to provide a drug delivery device comprising such a drive mechanism and comprising a cartridge sealed with a piston and being operably engaged with a piston rod of such drive mechanism. The drug delivery device should be rather easy and intuitive to handle.

SUMMARY OF THE INVENTION

In a first aspect a drive mechanism for a drug delivery device is provided for dispensing of a dose of a medicament. The drive mechanism comprises a housing extending in an axial direction. The housing may be of substantially tubular or cylindrical shape that allows gripping and operating of the drive mechanism, hence of the entire drug delivery device by one hand of a user. The housing may also be of rectangular or cubic shape which may smoothly fit into a palm of a user's hand.

The drive mechanism further comprises a piston rod to operably engage with a piston of a cartridge containing the medicament to be dispensed by the drive mechanism. The cartridge comprises a piston, which, by means of a displacement in axial distal direction, serves to expel an amount of the medicament from the cartridge corresponding to the axial displacement of the piston. The piston typically seals the cartridge in axial proximal direction. The piston rod serves to displace the piston of the cartridge in an axial distal direction. The piston rod is therefore operable to apply distally directed thrust or pressure to the piston of the cartridge for displacing the same in distal direction for a predetermined distance that corresponds to a respective amount of the medicament to be dispensed.

Furthermore, the drive mechanism comprises a drive spindle operably engageable with the piston rod during dose dispensing. The drive spindle is rotatably supported in the housing and is preferably axially fixed. It is exclusively operable to be rotated in a dose incrementing direction during setting of a dose and to rotate in an opposite, hence in a dose decrementing direction during dispensing of a dose. Preferably, the drive spindle is selectively engageable with the piston rod only during dose dispensing.

For dose setting drive spindle and piston rod are operably disengaged from each other. In this way, a required dose of the medicament can be set without any interaction with the piston rod. It is only during dose dispensing that the drive spindle is operably engaged with the piston rod for advancing the same in a distal, hence dose dispensing direction.

The drive mechanism is further equipped with a drive member axially displaceable relative to the drive spindle against the action of a spring element during dose setting. The drive member is threadedly engaged with the drive spindle to form a kind of a spindle gear. Preferably, the drive member is axially displaceable relative to the drive spindle and relative to the housing. The drive member is further rotatably locked to the housing and is therefore only allowed to slidably displace relative to the housing.

Since drive member and drive spindle are threadedly engaged, an axial displacement of the drive member relative to the drive spindle sets the drive spindle, which is axially fixed, in rotation. A dose setting axial displacement of the drive member is operable against the action of a spring element, typically in form of a compression spring. However, for dose dispensing or dose injection, the biased or tensioned spring element may serve as a drive element to return the drive member to its initial position.

Hence, during dose dispensing, the drive member will be axially displaced by the action of the spring thereby inducing a counter-directed rotation to the drive spindle. Since the drive spindle is operably engageable with the piston rod during such a dose dispensing rotation, the piston rod will advance accordingly.

By means of the mutual engagement of the axially displaceable drive member and the spring element, mechanical energy can be stored in the drive mechanism by inducing an axially-directed sliding motion onto the drive member. Hence, for setting of a dose an axially-directed sliding displacement of the drive member is generally sufficient.

Additionally and depending on the lead of the threaded engagement of drive member and drive spindle, different transmission ratios between the drive member and the drive spindle can be realised allowing to adapt the drive mechanism to different specific application scenarios. Since it is only the drive member which is biased by the spring element, a variety of different transmission ratios between drive member and drive spindle can be realised by implementing respective leads without the necessity to modify the spring element.

Preferably, the drive member is displaceable in axial proximal direction against the action of the spring element for setting of a dose. The drive spindle will then rotate in a dose incrementing direction. For dose correction or during dose dispensing, which comes along with a decrementing of a set dose, the drive member is driven in distal direction under the action of the spring element. Consequently and due to the threaded engagement of drive member and drive spindle, the drive spindle then rotates in the opposite, hence in a dose decrementing or dose dispensing direction.

In a further embodiment, the drive member comprises a hollow sleeve portion threadedly engaged with the drive spindle and further comprises an axially extending toothed rack portion. Typically, the hollow sleeve portion and the toothed rack portion are separated from each other in radial direction by means of an interconnecting bar. In axial direction the hollow sleeve portion and the toothed rack portion may at least partially overlap.

The hollow sleeve portion comprises an inner thread to engage with an outer thread of the drive spindle. In this way, axially-directed displacement of the drive member relative to the drive spindle induces a dose incrementing or dose decrementing rotation of the drive spindle. The toothed rack portion is typically of elongated shape and extends in axial-direction featuring a number of teeth arranged side-by-side in axial-direction to mate with a pinion of a dose mechanism or of a dose setting member. The design of the drive member with the hollow sleeve portion and the radially-offset toothed rack portion enables a rather flat or slim design of the housing of the drive mechanism since toothed rack portion and hollow sleeve portion may be arranged next to each other as seen in radial direction.

In a further embodiment the drive mechanism also comprises a dose setting member rotatably mounted to a sidewall of the housing. The dose setting member is preferably operably engageable with the drive member, in particular with its toothed rack portion. Arranging a dose setting member to a sidewall of the housing provides a very intuitive and easy handling of the drive mechanism for setting of a dose as well as for displaying the size of a set dose to a user. Integration of the dose setting member into the sidewall of the housing is also beneficial for a rather flat-shaped, rectangular or cubic design of the housing. Given that the housing comprises a substantially rectangular cross-section perpendicular to the axial direction, the dose setting member may be mounted to or in the larger sidewall portion of the rectangular cross-section.

In a further embodiment the rack portion of the drive member is engaged with a pinion of a gear wheel. Typically, the gear wheel is further operably engaged with the dose setting member. The gear wheel may be directly engaged with the dose setting member. It may be a component of the dose setting member or it may be operably engaged with the rotatable dose setting member, e.g. by some kind of transmission gear.

For instance, a rack and pinion gear can be provided for transferring a rotatable displacement of a gear wheel of a dose setting arrangement into an axial sliding displacement of the drive member against the action of the spring element. The gear wheel engaged with the rack portion and/or a respective transmission gear may also support a rather flat design of the drive mechanism and its housing.

In another embodiment, the drive member is axially slidably disposed in the housing from above. For this purpose, the drive member and the housing may comprise mutually engaging guiding structures supporting a well-defined axial displacement of the drive member relative to the housing. For instance, the drive member may comprise a ridge portion protruding from a lateral side of the toothed rack portion which is slidably received in a correspondingly-shaped guiding structure of the housing. Moreover, also the hollow sleeve portion may comprise a radially outwardly extending protrusion to engage with a correspondingly-shaped groove of the housing.

Preferably, both, the toothed rack portion as well as the sleeve portion of the drive member comprise a guiding structure which is operable to engage with a correspondingly-shaped axially extending guiding structure of the housing, respectively. In this way, both portions of the drive member hence rack portion and sleeve portion can be separately and securely guided in the housing. By a twofold sliding support of the drive member in the housing, an axial displacement of the drive member relative to the housing effectively free of tilt or cant can be effectively provided.

In a further embodiment, the drive member is axially displaceable relative to the housing between a distal stop and a proximal stop. Hence, axially-directed displacement of the drive member relative to the housing is delimited in both axial directions. In this way, a dose incrementing as well as a dose decrementing axial displacement of the drive member relative to the housing can be confined between predefined margins.

Typically, the distal stop corresponds to a zero dose configuration whereas the proximal stop correlates to and defines a maximum dose configuration, which in case of a drive mechanism for an insulin injecting device may correspond to 120 I.U. By means of the proximal stop, a maximum dose to be set can be effectively limited. When the drive member engages and abuts with the proximal stop, a further proximally-directed displacement of the drive member can be effectively impeded. Since the drive member is typically engaged with a gear wheel of the dose setting member, a further dose incrementing rotation of the dose setting member is effectively blocked.

Moreover, due to the axially delimited displacement of the drive member relative to the drive spindle also a further dose incrementing rotation of the drive spindle is effectively impeded or blocked.

When reaching the opposite distal stop configuration, which may correspond to a zero dose configuration, either the distal stop itself or an additional clicking member may audibly interact with the drive member in order to generate an audible click sound indicating to a user, that the end of a dose dispensing procedure has been reached and that dose dispensing has just terminated.

The distal stop and/or the proximal stop typically provided by the housing may preferably engage with the hollow sleeve portion of the drive member. In typical embodiments, proximal stop and distal stop of the housing may be arranged at respective proximal and distal ends of a groove of the housing which is adapted to slidably receive a radially outwardly extending protrusion of the sleeve portion of the drive member. With such an implementation, the radially outwardly extending protrusion of the hollow sleeve portion provides a double function. It serves to axially guide the drive member relative to the housing and to define proximal and distal stop positions of the drive member relative to the housing.

In a further embodiment, the spring element comprises a compression spring extending around the drive spindle. In this way, a nested or interleaved arrangement of spring element, drive spindle and drive member can be obtained. Preferably, the spring element also at least partially extends around the drive member. In this way, the spring element and the drive member may mutually stabilise to support a smooth axial displacement of the drive member relative to the drive spindle.

In a further embodiment, the spring element axially extends between the drive member and the drive spindle. Here, the drive spindle may comprise a radially outwardly extending rim or flange portion, which may serve as a proximal stop for the spring element. Preferably also the drive member comprises a correspondingly-shaped radially outwardly extending rim to receive an opposite end of the spring element.

The spring element may be positively engaged with the drive member and/or with the drive spindle. However, a mutual axial abutment of the opposite axial end sections of the spring element to respective radially outwardly extending rim portions or flange portions of drive spindle and drive member may be sufficient to keep the spring element in place. Moreover, it is intended that the spring element is tensioned to a minimum degree when the drive member is in its distal stop position.

Additionally and according to a further embodiment, the drive spindle comprises a toothed rim rotatably engaged with a ratchet member. The toothed rim is preferably provided at a proximal end of the drive spindle. The toothed rim may equally serve as a radially outwardly extending flange portion adapted to axially support a proximal end of the spring element. Preferably, the toothed rim of the drive spindle is rotatably engaged with a ratchet member. In this way rotation in dose incrementing and/or dose decrementing direction of the drive spindle can be rotatably locked or rotatably secured by the ratchet member.

Therefore, a proximally-directed displacement of the drive member against the action of the spring can be locked in place since the drive spindle threadedly engaged with the sleeve portion of the drive member is effectively hindered by the ratchet member to rotate freely.

The ratchet member serves to provide a clutch mechanism operable to lock a rotational movement of the drive spindle. In this way, mechanical energy can be stored in the spring element when compressed by the proximally-directed displacement of the drive member relative to the drive spindle or relative to the housing.

Preferably, the ratchet member is configurable to selectively interlock or to release the toothed rim of the drive spindle. In an interlocking configuration, the drive spindle is rotatably locked by the ratchet member. However, in a release configuration, the toothed rim and hence the drive spindle is free to rotate relative to the latch element and relative to the housing. Then, mechanical energy stored in the tension spring element can be released because the drive spindle is free to rotate, thereby allowing the drive member to be displaced in distal direction under the action of the previously-tensioned spring element.

In another embodiment, the ratchet member comprises at least one arc-shaped latch element which is variably stressable in radial direction to selectively engage or disengaged with the toothed rim of the drive spindle. Releasing and interlocking of the drive spindle and the ratchet member may be exclusively obtained by a modification of the latch element of the ratchet member.

Preferably, the latch element is either pivotally supported in radial direction or it is resiliently deformable in radial direction to engage with the toothed rim of the drive spindle with variable and adjustable strength. Hence, by modifying a degree of engagement of the latch element with the toothed rim of the drive spindle, rotation of the drive spindle can either be interlocked or released, respectively.

Moreover, by means of a variably stressable latch element of the ratchet member also intermediate configurations are conceivable, in which the toothed rim and the drive spindle are generally allowed to rotate while still being in mechanical engagement with the latch element. In such configurations, the latch element only partially and/or gradually obstructs the rotational movement of the drive spindle, thereby retarding the angular velocity of the drive spindle, e.g. during a dose dispensing procedure. Consequently, an angular velocity of the drive spindle can be regulated or modified by means of the ratchet member.

It is generally conceivable, that the ratchet member comprises several latch elements homogeneously distributed around the outer circumference of the ratchet member. Typically, the ratchet member comprises a cup-shaped receptacle to receive the toothed rim of the drive spindle therein. The arc-shaped latch element then forms a portion of the sidewall of the cup-shaped ratchet member or it is integrated into the sidewall of the ratchet member.

In another embodiment the dose setting member is rotatably engaged with a first dose indicating wheel and with a second dose indicating wheel to display at least first and second digits of a number in a dose indicating window of the housing. First and second dose indicating wheels may be coaxially arranged in the housing of the drive mechanism. First and second dose indicating wheels may be of disc-like shape and may feature a series of dose indicating numbers at an outer side face thereof. Hence, the axis of rotation of the first and second dose indicating wheel will be radially offset from the dose indicating window of the housing.

The first dose indicating wheel may be adapted to display numbers 0-9, whereas the second dose indicating wheel may display numbers from 0-12, thereby representing together the numbers 0, 1, 2, 3, 4, up to 119 and 120. First and second dose setting members are typically geared, e.g. by mutually engaging sprockets and pinions. First and second dose indicating wheels may either be directly geared or there may be provided at least one additional gear wheel that serves to provide a required transmission ratio between first and second dose indicating wheels.

Transmission of a rotational movement to the second gear wheel is typically provided by a gear wheel having a reduced number of cogs that are separated from each other in such a way, that the second gear wheel is rotated one step further every time the first gear wheel has rotated by an angular distance that corresponds to an interval of 10 digits.

According to another embodiment, the drive mechanism further comprises a pinion fixed to a distal end of the drive spindle. Said pinion is further geared with a drive sleeve rotatably supported in the housing. In this way, a dose incrementing as well as a dose decrementing rotation of the drive spindle can be directly transferred to a drive sleeve. The drive sleeve comprises a hollow shape and is adapted to receive the piston rod therein. Since the pinion is geared with the drive sleeve, the drive spindle and the drive sleeve can be arranged radially offset, thereby allowing for a rather flat but laterally elongated design of the drive mechanism and its surrounding housing.

Preferably, the drive sleeve is arranged at a radial offset from the drive spindle facing away from the radially outwardly extending toothed rack portion of the drive member. Axial dimensions of the pinion and the gear wheel or geared rim of the drive wheel is such that the drive sleeve is axially displaceable relative to the pinion and hence relative to the drive spindle to a certain extent. By means of an axial displacement of the drive sleeve, a clutch mechanism can be implemented, by way of which the drive mechanism can be switched between a dose setting configuration and a dose dispensing configuration.

In a further embodiment, the drive sleeve is axially displaceable between a distal stop position and a proximal stop position. In its distal stop position, the drive sleeve is rotatably engaged with the piston rod in order to drive the same in distal direction. However, in the proximal stop position, the drive sleeve is disengaged from the piston rod. In this way, the drive sleeve may rotate with the drive spindle during a dose setting procedure without any impact on the piston rod. It is only due to the distally-directed displacement of the drive sleeve, that a respective clutch mechanism is activated.

The clutch mechanism provides a double function. In a first aspect, the clutch mechanism serves to operably engage the drive sleeve with the piston rod. In a second aspect, the clutch mechanism serves to release the drive spindle from the ratchet member. Since drive sleeve and drive spindle are permanently geared, in both, the dose dispensing configuration as well as in the dose setting configuration, a release of the drive spindle may lead to a dose decrementing rotation of the drive spindle, which is transferred to a respective rotation of the drive sleeve by means of the pinion located at the distal end of the drive spindle.

The twofold function of the clutch mechanism is preferably operable sequentially. During switching of the drive mechanism from the dose setting mode into the dose dispensing mode, a mutual engagement of drive sleeve and piston rod is to be established before a rotation of the drive spindle relative to the housing or relative to the drive member is allowed. In this way, mechanical energy stored in the spring element biased by the axially displaceable drive member can be saved and is therefore effectively hindered to dissipate in a rather uncontrolled way.

In a further embodiment, the drive mechanism also comprises an axially displaceable dose dispensing button located at a proximal end of the housing. Distally-directed displacement of the dose dispensing button, which is typically conductible by a thumb of a user, may activate the clutch mechanism in order to rotatably engage drive sleeve and piston rod and in order to release the ratchet mechanism of the drive spindle.

The dose dispensing button is typically depressible in distal direction against the action of another spring element, e.g. an injection spring. A respective spring element may for instance be disposed axially between an inside facing portion of a proximal end face of the dose dispensing button and a proximal end face of the ratchet member.

Here, it may be of particular benefit, when the dose dispensing button separately engages with the ratchet member and with the drive sleeve for switching the drive mechanism from a dose setting mode into a dose dispensing mode.

The dose dispensing button may particularly extend across the entire cross-section of the rectangular-shaped housing. The dose dispensing button may comprise a hollow cupped shape to receive the compression spring, by way of which the dose dispensing button can be axially biased with respect to the ratchet member.

Additionally, the dose dispensing button may comprise a distally extending strut or a respective extension, to directly engage with a proximally-facing flange portion of the drive sleeve. By means of the distally extending strut, the drive sleeve can be displaced in distal direction by a distally-directed depression of the dose dispensing button, e.g. against the action of the injection spring. The drive sleeve may be additionally engaged with another spring element which serves to return the drive sleeve into its proximal stop position as soon as a distally-directed thrust exerted by the dose dispensing button is no longer present.

Generally, by means of the spring element operably engaged with the drive member, a semi-automated drug delivery device can be provided. During a dose setting procedure the spring element can be strained or tensioned to such a degree, that a dose dispensing action of the drug delivery device can be exclusively driven by the relaxing action of the biased spring element. Hence, dose dispensing is completely governed by the action of a spring element previously tensioned and strained in a dose setting procedure.

According to another aspect, the invention also relates to a drug delivery device for dispensing of a dose of a medicament. The drug delivery device comprises a drive mechanism as described above and a cartridge at least partially filled with the medicament to be dispensed by the drug delivery device. The cartridge is arranged in the housing of the drive mechanism or in a cartridge holder of the drug delivery device which is fixed to the housing either releasably or non-releasably. Consequently, the drug delivery device comprises a cartridge holder to receive and to accommodate a cartridge filled with the medicament.

In case of a disposable drug delivery device the cartridge is not to be replaced when empty but the entire device is intended to be discarded. With a reusable device, the drive mechanism can be reset and an empty cartridge can be generally replaced by a new one.

In the present context, the distal direction points in the direction of the dispensing and of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, various embodiments of the invention will be described by making reference to the drawings, in which.

DETAILED DESCRIPTION

Figure 1:
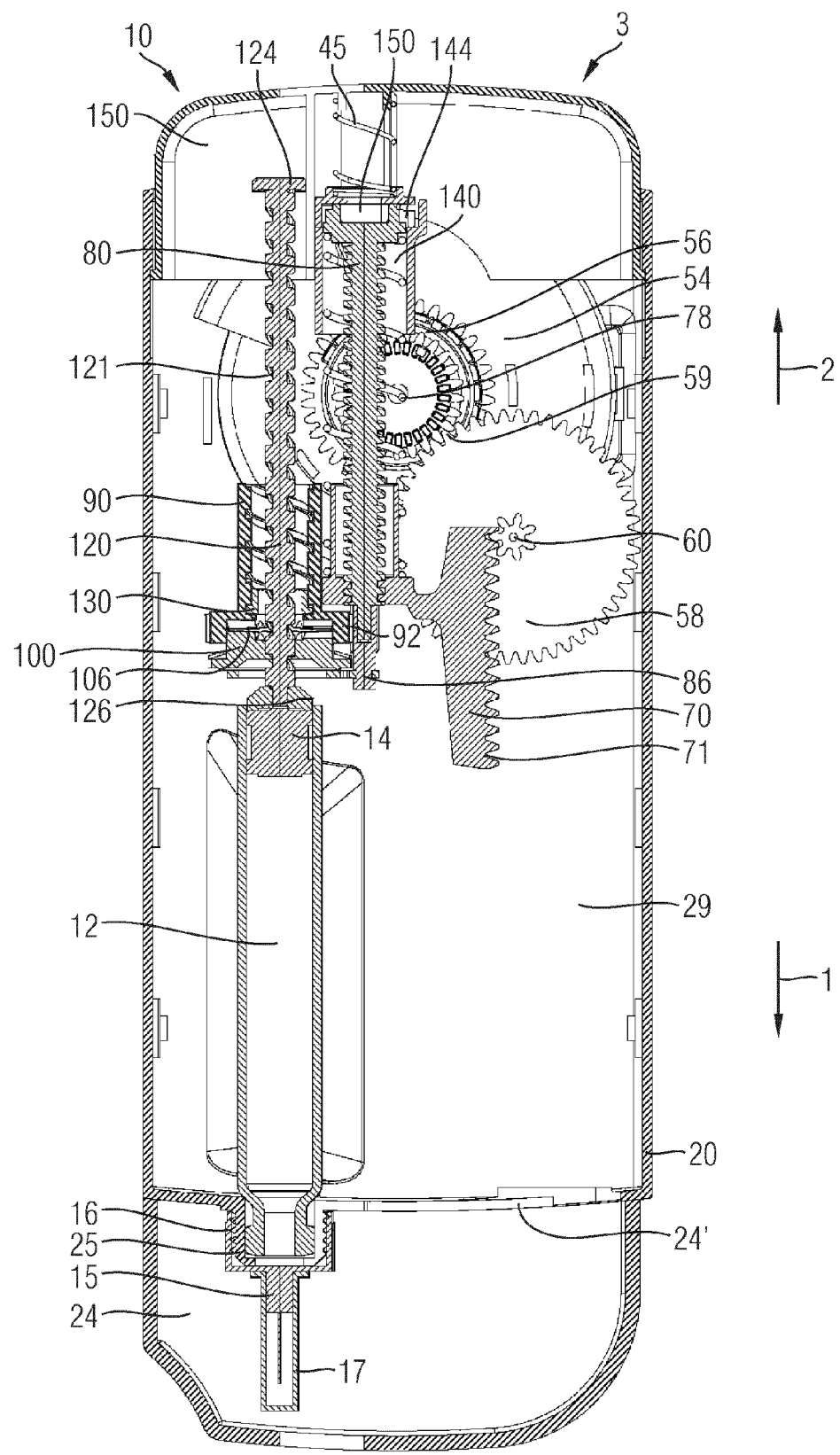
FIG. 1 schematically illustrates a front view of the drug delivery device.
Figure 2:
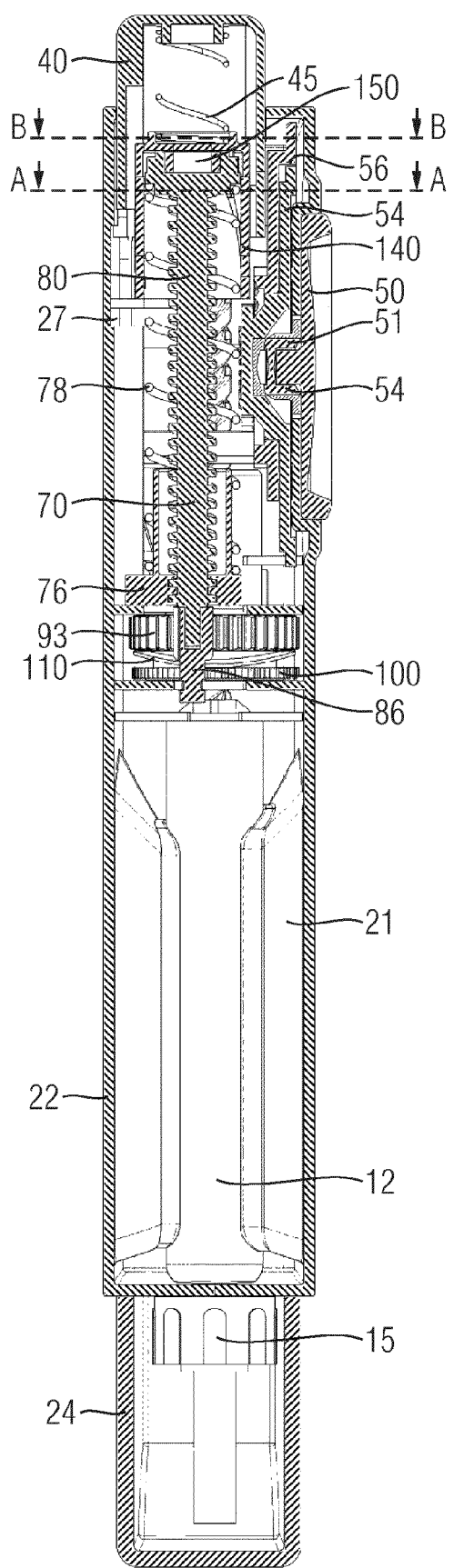
FIG. 2 shows a side view of the drug delivery device.
Figure 3:
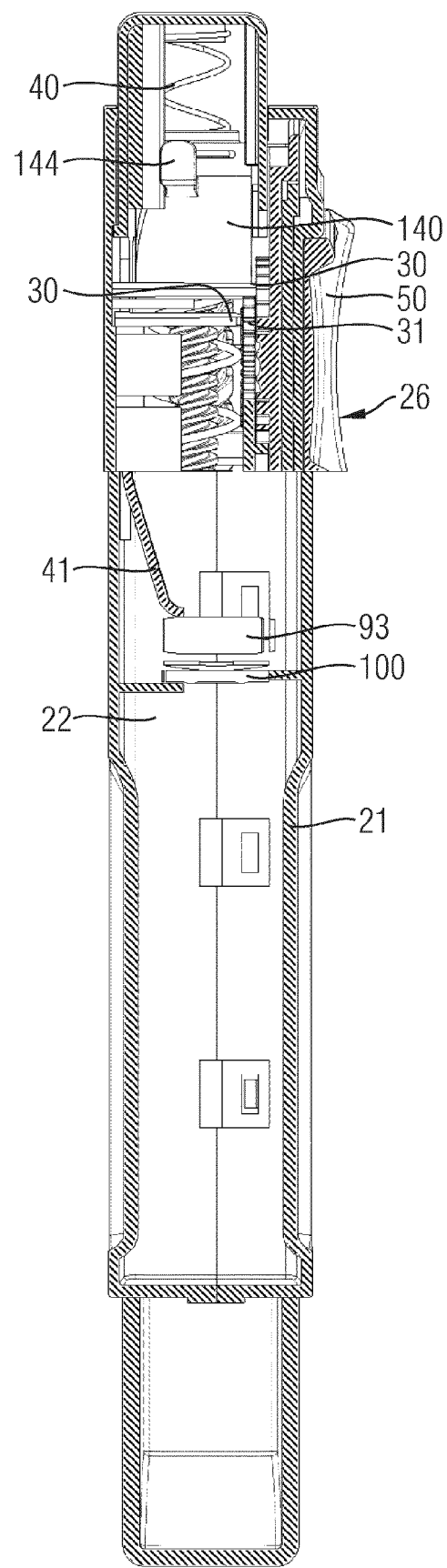
FIG. 3 shows another side view as seen from the opposite side compared to FIG. 2.

As illustrated in FIGS. 1 and 2 the drug delivery device 10 comprises a rather rectangular or cubic-shaped housing 20 comprising an upper housing portion 21 and a lower housing portion 22. In the present embodiment, the upper housing portion 21 may serve as a mounting base to assemble the components of the drive mechanism 3 thereon. The lower housing portion 22 may then serve as a cover, which preferably stabilises and keeps the various components of the drive mechanism 3 at their positions. However, the roles of upper and lower housing portions may also be interchanged in alternative embodiments.

The rectangular shape of the housing 20 is particularly adapted to take and to clasp the device 10 by one hand of a user. The drug delivery device 10 therefore comprises an elongated shape extending in axial direction. In the present context, the axial distal direction is denoted with reference number 1 and the opposite proximal direction is denoted with reference number 2. The housing 20, in particular both of its halves 21, 22, comprises a cartridge window 23.

The cartridge window 23 may comprise a recess in the upper and/or lower housing portion 21, 22 and may be at least partially transparent to allow visual inspection of a filling level of a cartridge 12 assembled inside the housing. The distal end of the housing 20 is further provided and protected by a removable cap 24. The cap 24 may positively engage with a distal end of upper and lower housing portions 21, 22 in order to protect a threaded socket 25 formed by upper and lower housing portions 21, 22.

Figure 6:
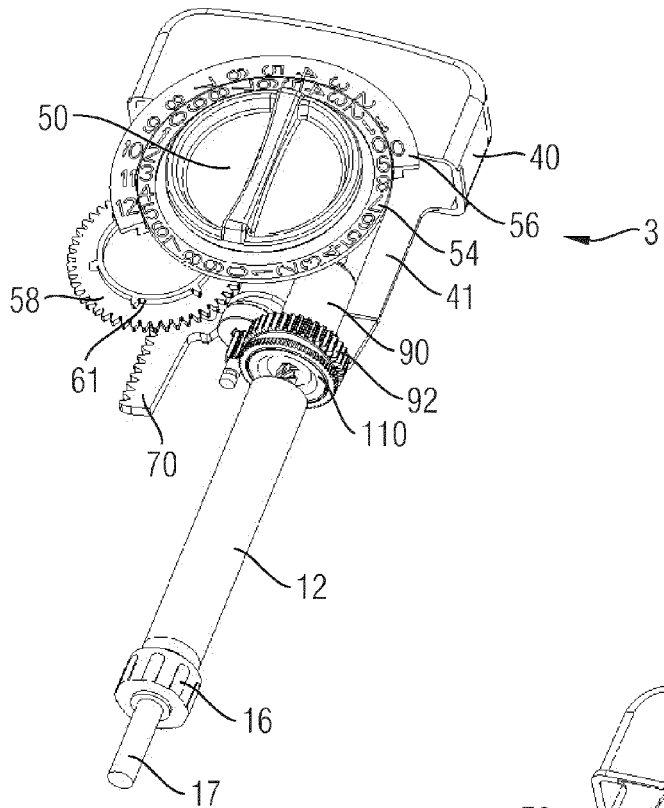
FIG. 6 shows a perspective isolated view of a dose indicating arrangement as seen from the front.
Figure 7:
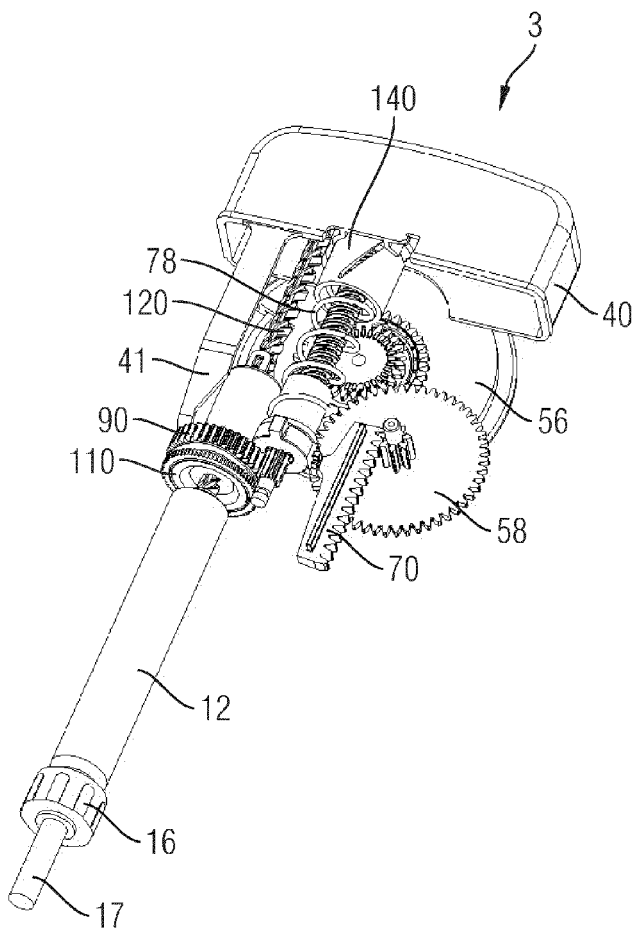
FIG. 7 shows the dose indicating arrangement according to FIG. 6 from the back side.
Figure 8:
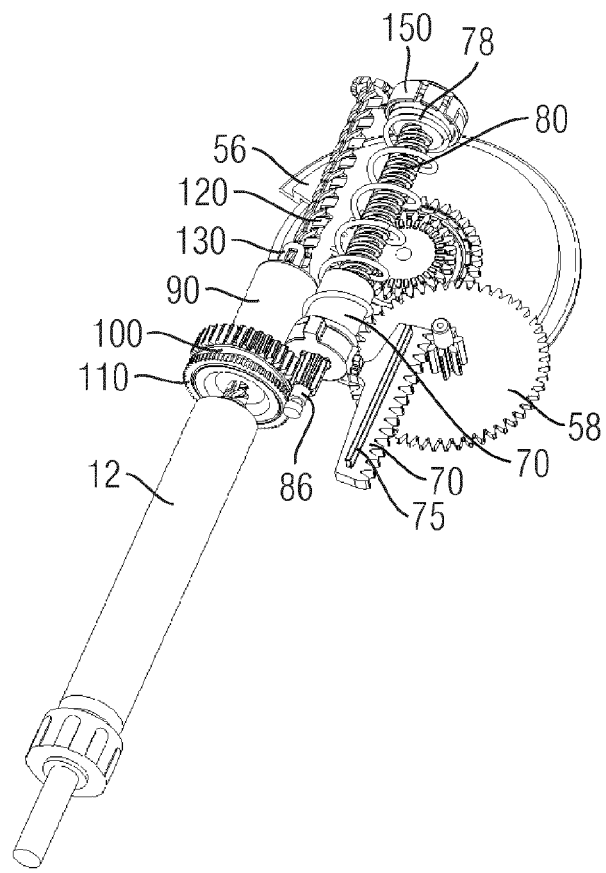
FIG. 8 shows an enlarged view of the dose indicating and dose setting arrangement according to FIG. 7.

The threaded socket 25 is adapted to receive a needle assembly 15, in particular a cup-shaped needle hub 16 providing a double-tipped injection needle. In the various Figures, in particular in FIGS. 1, 2 and in FIGS. 6 and 7, the needle assembly 15 is illustrated with a needle cap 17, which is to be removed from the needle assembly 15 prior to conducting a dose dispensing procedure. The cartridge 12 to be fixed in the housing 20 comprises a tubular-shaped barrel filled with a medicament to be dispensed by the drug delivery device 10.

The barrel is sealed in proximal direction 2 by means of a piston 14, which is slidably disposed in axial direction 1, 2 inside the barrel of the cartridge 12. The piston 14 of the cartridge 12 is operably engageable with a piston rod 120. The piston rod 120 of the drive mechanism 3 is operable to apply distally-directed thrust or pressure to the piston 14 in order to drive the same in distal direction 1. In this way, a fluid pressure may build up inside the cartridge 12.

When the distal dispensing end of the cartridge 12 is connected with the needle assembly 15 in such a way, that a proximally extending tipped portion of the needle penetrates a distally-located seal of the cartridge, e.g. a septum, a predefined amount of the medicament can be expelled from the cartridge 12 via the needle assembly 15 and into biological tissue.

Figure 5:
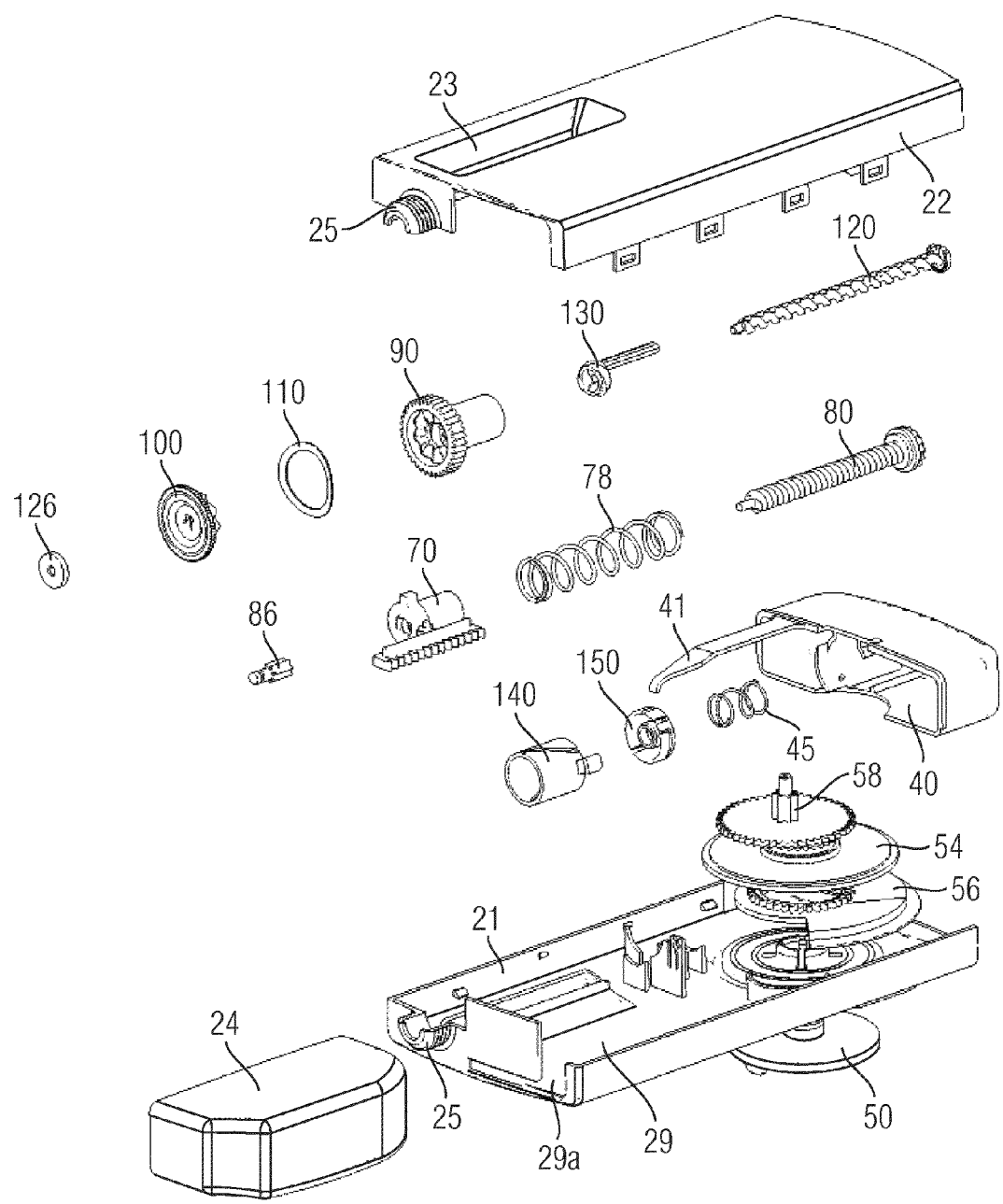
FIG. 5 is an exploded view of the components of the drive mechanism.

As indicated in FIG. 1, the housing 20 comprises a compartment 29 adapted to receive the protective cap 24. For this purpose, the distal end face of the housing 20 comprises a slit 29a as indicated in FIG. 5 allowing to slidably receive the protective cap therein. Here, the slit 29a may serve as a hinge to pivot and to slidably receive the cap 24 when the device is in use. In this way, the cap 24 is non-removably attached to the housing 20 and cannot get lost.

In the following, setting of a dose is described.

For setting of a dose, the user typically takes or clasps the housing 20 in one hand and starts to rotate, in particular to dial a dose setting member 50 located in the upper housing portion 21. The dose setting member 50 as illustrated in detail in FIG. 10 comprises a circular-shaped button comprising an outer rim and a central gripping bar 52 extending across the disc-shaped dose setting member 50. The gripping bar 52 divides the dose setting member 50 into two recesses allowing for an intuitive and easy gripping thereof.

Figure 10:
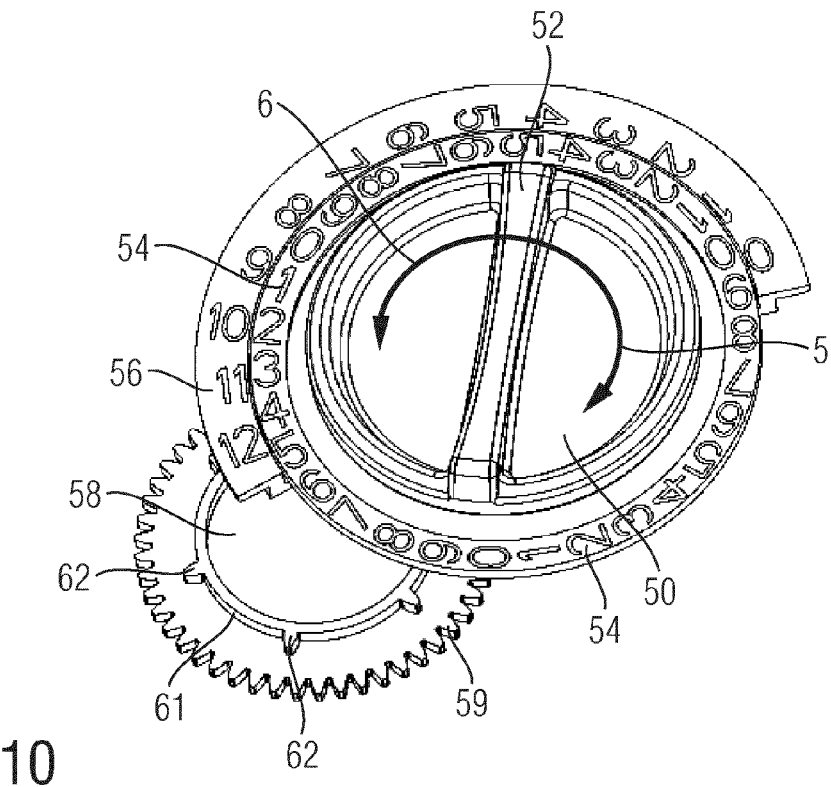
FIG. 10 is an isolated view of the interleaved first and second dose indicating wheels as seen from the front.
Figure 11:
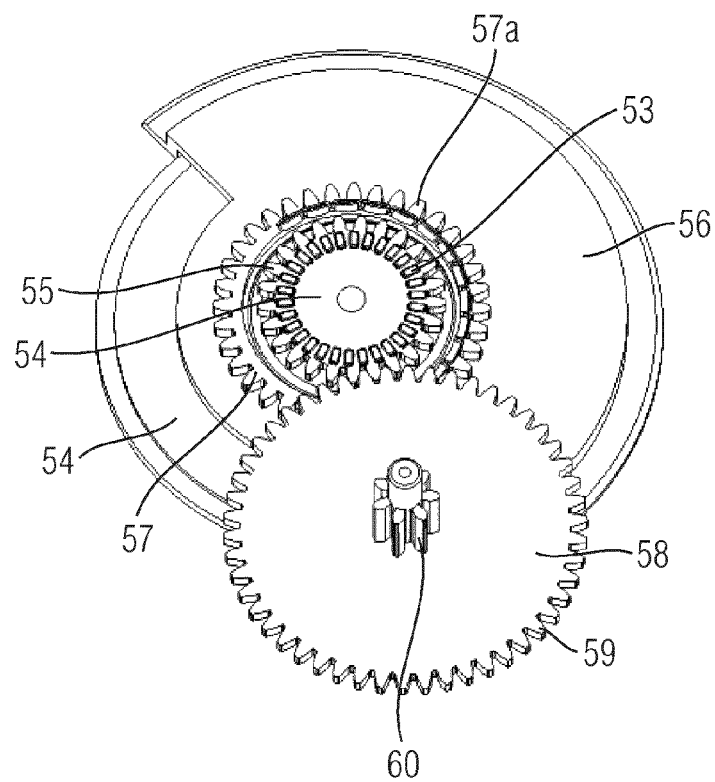
FIG. 11 shows the wheels according to FIG. 10 from the back side.

As indicated by the arrows in FIG. 10, the dose setting member 50 can be rotated either clockwise 5, e.g. in a dose incrementing way or counter-clockwise, e.g. in a dose decrementing way for incrementing or decrementing a dose to be dispensed by the drug delivery device 10. The dose setting member 50 is directly coupled to a dose indicating arrangement as illustrated in FIGS. 10 and 11. The dose setting member 50 as illustrated in cross-section of FIG. 12 is rotatably coupled with a dose indicating wheel 54.

Figure 12:
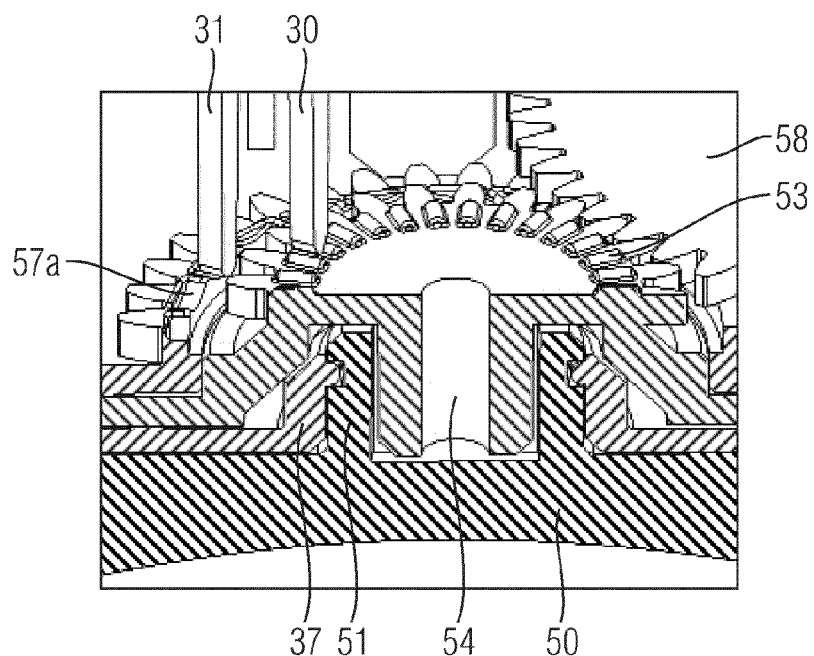
FIG. 12 shows a perspective and partially cut view of the dose indicating wheels assembled in the housing.

As indicated in FIG. 12, the dose indicating wheel 54 comprises an axially extending shaft received in a correspondingly-shaped receptacle of the dose setting member 50. Even though not illustrated, the shaft and the receptacle are splined. Shaft and receptacle of the dose indicating wheel 54 and the dose setting member 50 comprise at least one protrusion engaged with a correspondingly-shaped groove.

As further illustrated in FIG. 12, the receptacle 51 of the dose setting member 54, in particular its sidewall is positively engaged with an inwardly extending fixing rim of the housing 20, thereby fixing the dose setting member 50 in axial direction relative to the housing 20 but allowing the dose setting member 50 to rotate in either direction relative to the housing 20.

The dose indicating wheel 54 serves as a first dose indicating wheel and comprises a series of dose indicating numbers at its outer circumference as illustrated in FIG. 10. Here, the dose setting member 50 and the first dose indicating wheel 54 are coaxially aligned. The dose indicating wheel 54 may feature an outer rim substantially enclosing the outer circumference of the dose setting member 50.

Figure 25:
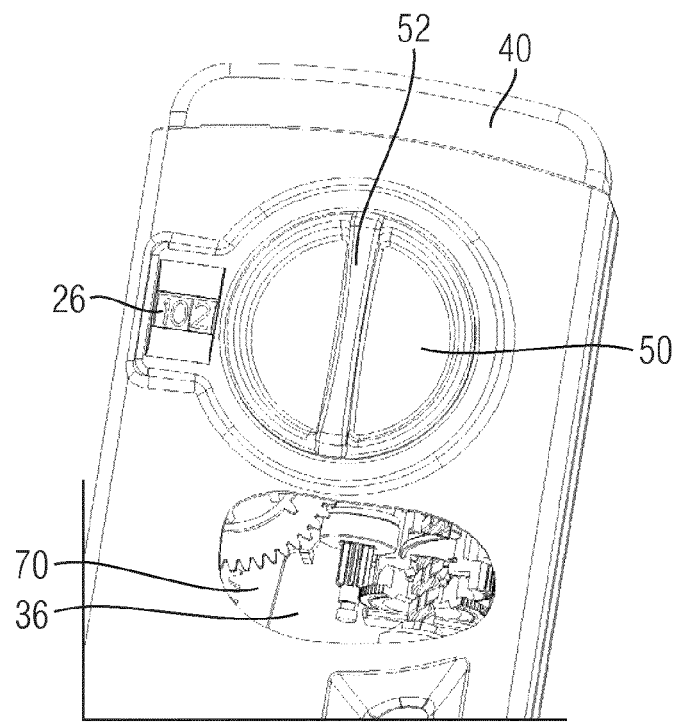
FIG. 25 shows a partially cut view of the assembled drug delivery device.

Due to the splined and direct engagement of the dose setting member 50 and the first dose indicating wheel 54, a rotation of the dose setting member 50 in either direction directly transfers to a respective rotation of the first dose indicating wheel 54. As a consequence, a respective number printed on a side of the dose indicating wheel 54 shows up in a dose indicating window 26 of the housing 20 as illustrated in FIG. 25.

The first dose indicating wheel 54 comprises a sprocket 55 to engage with an outer geared rim 59 of a gear wheel 58. The gear wheel 58 as illustrated in FIG. 11 comprises a further sprocket or pinion 60 axially offset from the geared rim 59 of the gear wheel 58. As will be explained later on, the sprocket 60 is engaged with a toothed rack portion 71 of a drive member 70.

On the side opposite to the sprocket 60 the gear wheel 58 comprises a rim structure 61 featuring isolated and separated cogs 62. Said cogs 62 are operable to engage with a geared rim 57 or sprocket of a second dose indicating wheel 56. As illustrated in FIGS. 10 and 11, the second dose indicating wheel 56 provides a second series of ten digit representing numbers of 10, 20, 30 and so on. By means of the isolated and circumferentially separated cogs 62, a stepwise incrementing rotation of the second dose indicating wheel 56 can be attained when the first dose indicating wheel 54 rotates.

In effect, by means of the two dose indicating wheels 54, 56 all numbers of for instance between 0 and 120 can be illustrated in the dose indicating window 26 of the housing 20. Implementation of the two interleaved dose indicating wheels 54, 56 allows for a rather large scale display so that even persons suffering impaired vision are enabled to read the illustrated numbers.

The first and the second dose indicating wheels 54, 56 further comprise a crown wheel 53, 57a engaging with clicking members 31, 30 provided on the inside of the oppositely disposed housing portion 21. As illustrated in FIG. 12, an inwardly extending pin-shaped clicking member 31 engages with a crown wheel 53 located on a side face of the first dose indicating wheel 54. Correspondingly also the second dose indicating wheel 56 comprises a crown wheel 57a to mate with a correspondingly-shaped clicking member 30 of the housing 20.

Mutual engagement of the first and second dose indicating wheels 54, 56 with respective clicking members 31, 30 provides an audible click sound when the dose setting member 50 is rotated either in dose incrementing direction or in dose decrementing direction. In this way, an audible feedback can be provided to the user when dialling the dose setting member 50 in either direction.

As illustrated for instance in FIGS. 7, 8, 19 and 20 the centrally-located sprocket 60 of the gear wheel 58 meshes with a toothed and elongated rack portion 71 of a drive member 70. The drive member 70 is axially displaceable relative to a drive spindle 80 extending therethrough. The drive member 70 comprises a sleeve portion 72 to receive the drive spindle 80, which is axially fixed in the housing 20 by means of a bearing 33 as for instance illustrated in FIGS. 13 and 20.

Figure 15:
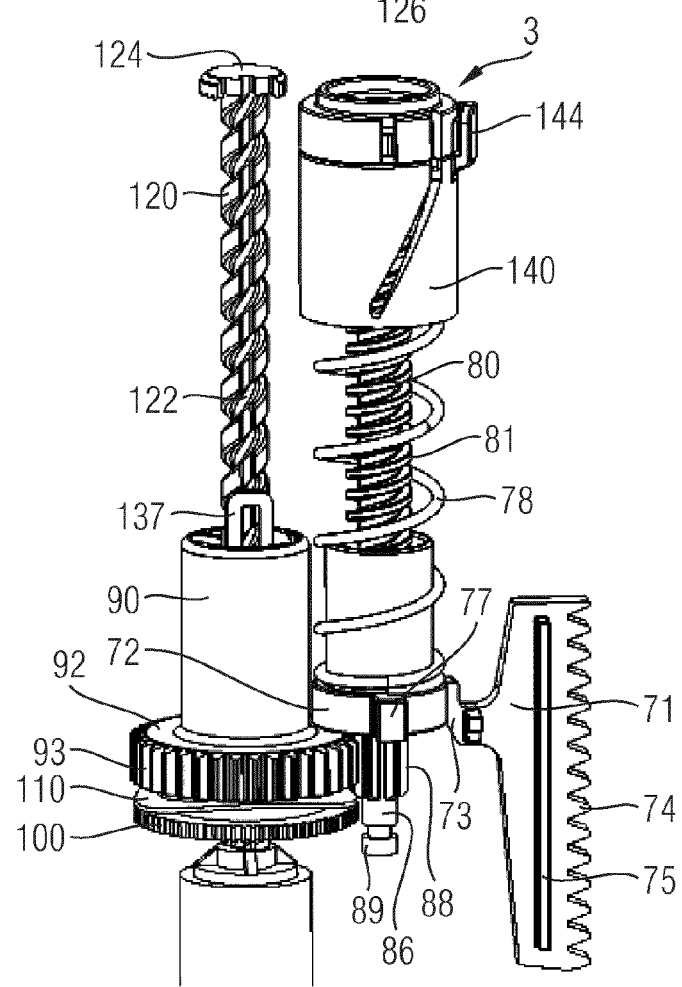
FIG. 15 is a perspective view of the mutual engagement of drive sleeve, drive spindle and drive member.

As illustrated in detail in FIG. 15, the toothed rack portion 71 is connected with the sleeve portion 72 via an interconnecting bar 73. The toothed rack portion 71 therefore radially outwardly extends from the sleeve portion 72 of the drive member 70. The drive member 70 is axially displaceable relative to the drive spindle 80 and relative to the housing 20 against the action of a spring element 78.

As illustrated in FIG. 15, the spring element 78 helically winds around the drive spindle 80. The spring element 78 is preferably designed as a compression spring and can be tensioned by an upward, hence proximally-directed displacement of the drive member 70 relative to the drive spindle 80. As further illustrated in FIG. 15, the sleeve portion 72 of the drive member 70 comprises a radially outwardly extending rim 76 at its distal end, which serves as a distal stop for the spring element 78.

Figure 13:
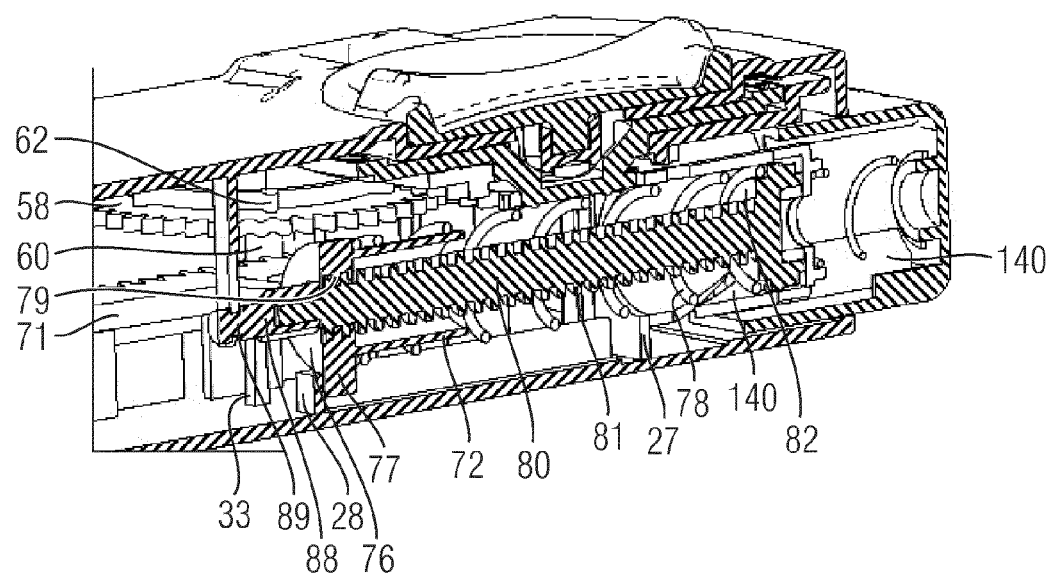
FIG. 13 shows a partially cut and perspective view of the drive spindle arranged in the housing.

Furthermore, the rim 76 comprises a radially outwardly extending protrusion 77 by way of which the drive member 70 can be axially guided relative to the housing 20. Moreover, the protrusion 77 may act as an axial stopper for the drive member 70. As shown in FIG. 13, the housing 20 comprises a proximal stop 27 and a distal stop 28 that are operable to engage with the radially outwardly extending protrusion 77 of the drive member 70. In this way, axial displacement of the drive member 70 relative to the housing 20 can be delimited in distal direction 1 as well as in proximal direction 2.

The drive member 70 is further threadedly engaged with the drive spindle 80. As illustrated in FIG. 13, the flange portion or rim 76 of the drive member 70 comprises an inner thread 79 engaging with an outer thread 81 of the drive spindle 80. Due to this threaded engagement and due to the axial fixing of the drive spindle 80 to the housing 20, a displacement of the drive member 70 in proximal direction 2 against the action of the spring element 78 comes along with a dose incrementing rotation 5 of the drive spindle 80.

Proximally-directed displacement of the drive member 70 relative to the housing 20 can be induced by a dose incrementing rotation of the dose setting member 50 and accordingly by a respective rotation of the gear wheel 58 and its sprocket 60. The axial length of the toothed rack portion 71 typically corresponds to the maximum distance the drive member 70 is allowed to be displaced in distal direction 1 according to the distance of the two stops 27 and 28.

Figure 4:
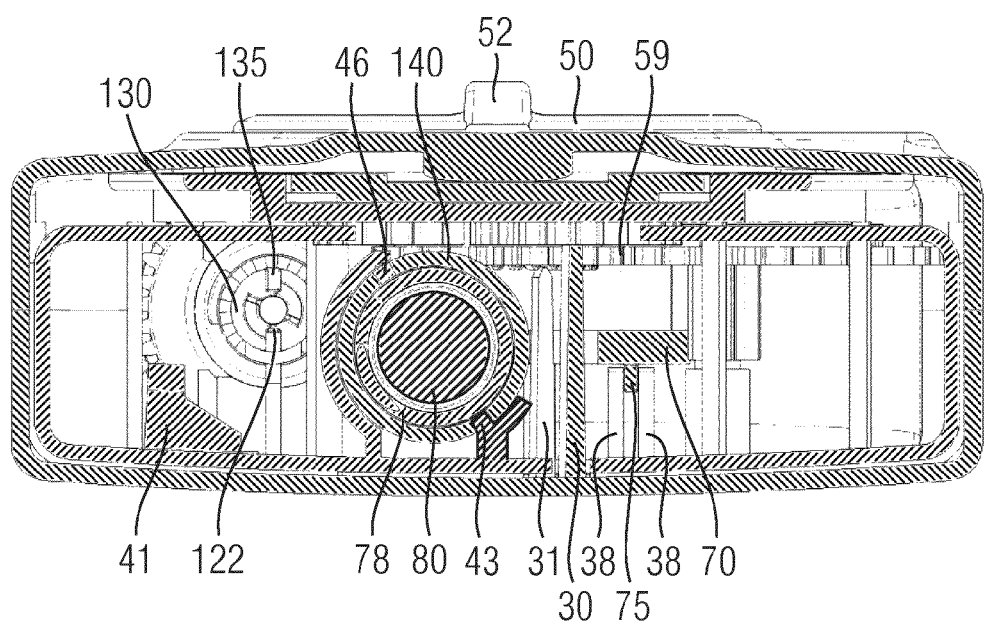
FIG. 4 shows a transverse cross-section through the drug delivery device according to A-A according to FIG. 2.

Additionally, as illustrated in FIGS. 4 and 15, there is provided a protruding ridge portion 75 on the side face of the toothed rack portion 71. Said ridge portion 75 can be guided in a guiding structure 38 of the housing 20 forming an elongated groove supporting the drive member 70 and guiding the drive member 70 in axial direction.

The toothed rack portion 71 comprises consecutive teeth 74 at its lateral side portion to engage with the sprocket 60 of the gear wheel 58.

Figure 9:
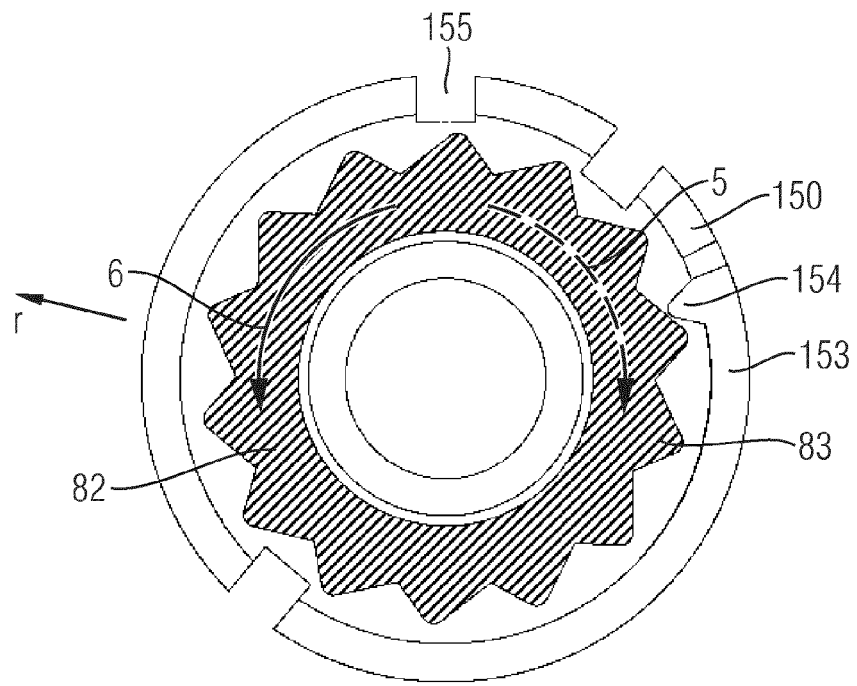
FIG. 9 shows a transverse cross-section B-B according to FIG. 2.

Drive member 70 and drive spindle 80 form a kind of a spindle gear. Proximally-directed displacement of the drive member 70 comes along with a tensioning of the spring element 78 thereby rotating the drive spindle 80 in a dose incrementing direction 5. The drive spindle 80 comprises a toothed rim 82 at its proximal end. As illustrated in cross-section of FIG. 9, said toothed rim 82 engages with a radially outwardly extending latch element 153 of a ratchet member 150. The cup-shaped ratchet member 150 receives the toothed rim 82 of the drive spindle 80 and inhibits a counter-directed, hence, a dose decrementing rotation 6 of the drive spindle 80.

For this purpose, the latch element 153 comprises an arc-shape and at least partially extends along the outer circumference of the toothed rim 82 of the drive spindle 80. The latch element 153 serves as a clutch element and the ratchet member 150 serves as a clutch member to selectively inhibit a rotation of the drive spindle 80. Typically, during dose setting, the latch or clutch element 153 meshes with a radially inwardly extending lug 154 with the teeth 83 of the toothed rim 82.

The latch element 153 is either pivotal in radial direction (r) and/or is resiliently deformable in radial direction to engage with the teeth 83 of the toothed rim 82 of the drive spindle 80. Depending on the slope and geometry of mutually engaging teeth 83 and the lug 154, a dose incrementing rotation 5 as well as a dose decrementing rotation 6 of the drive spindle 80 requires application of a respective actuation force above a predefined level or threshold.

The mutual engagement of the latch element 153 with the toothed rim 82 is in any case sufficient to counterbalance the relaxing force of a biased spring element 78. In this way, the ratchet member 150 is operable to keep the drive spindle 80 fixed, independent of the axial position of the drive member 70 and the degree of tension of the spring element 78.

The spring element 78 may abut with its proximal end at the radially outwardly extending toothed rim 82 of the drive spindle 80. In this way, the spring element 78 is axially constrained between the drive spindle 80 and the drive member 70.

Figure 20:
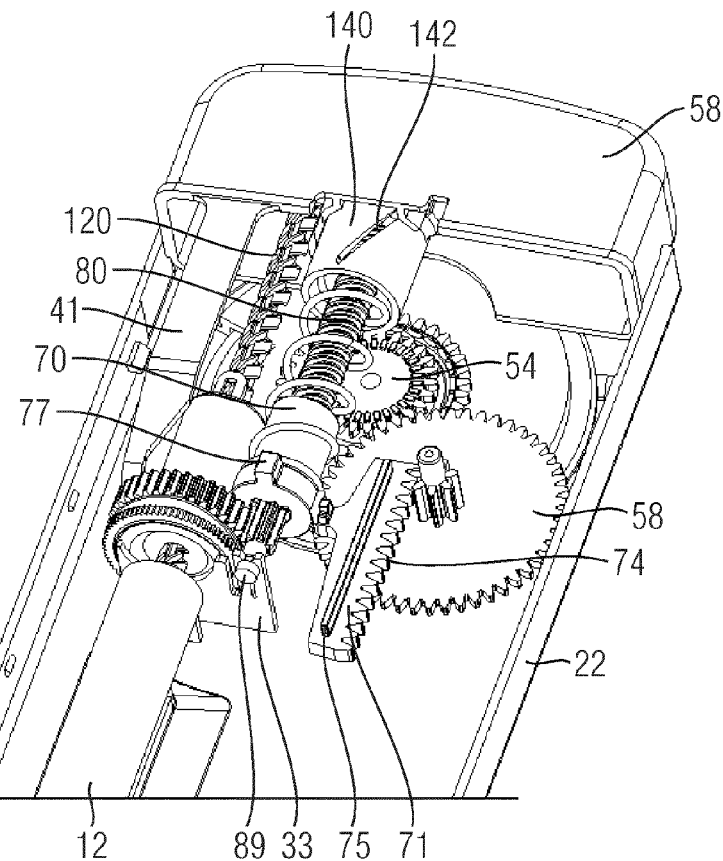

The distal end of the drive spindle 80 is provided with a pinion 86 featuring a bearing portion 89 in form of a circumferential groove or recess. As illustrated in FIGS. 13 and 20, the pinion 86 is supported by a bearing 33 of the housing 20, thereby axially and radially fixing the drive spindle 80 in the housing 20. The pinion 86 comprises various cogs or teeth 88 engaging with a geared rim 93 of a drive sleeve 90. The drive sleeve 90 as illustrated in detail in FIGS. 14 and 15 comprises a tubular-shaped sleeve portion and a radially extending flange portion 92 at its distal end.

The flange portion 92 is provided with a geared rim 93 that meshes with the pinion 86 of the drive spindle 80. Here, drive spindle 80 and drive sleeve 90 are permanently geared. Therefore, a dose incrementing as well as a dose decrementing rotation of the drive spindle 80 always leads to a corresponding rotation of the drive sleeve 90.

Furthermore, the drive sleeve 90 at least partially encloses the piston rod 120. The drive sleeve 90 is operably releasable from the piston rod 120 during dose setting but is operably engageable with the piston rod 120 for dispensing of a dose, as will be explained later on.

Figure 14:
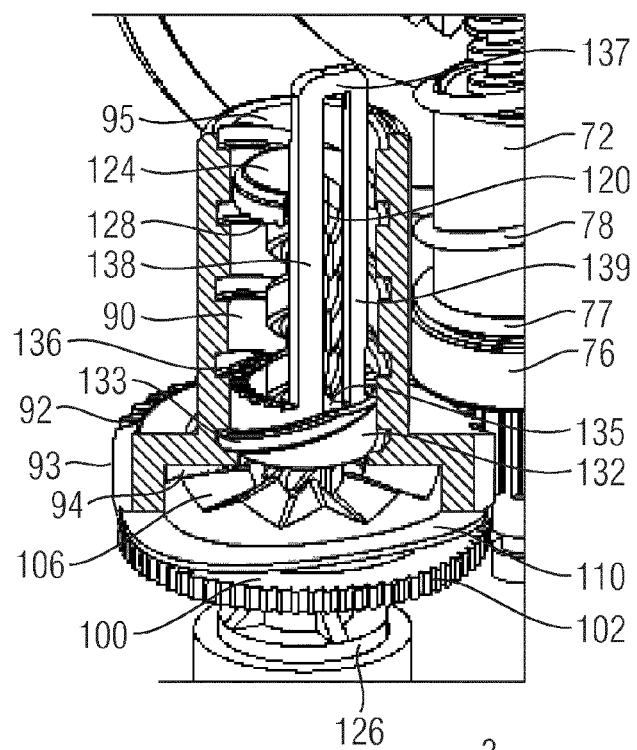
FIG. 14 is a partially cut- and enlarged view of the drive sleeve.

Radially sandwiched between the drive sleeve 90 and the piston rod 120 there is provided a dose limiting member 130. The dose limiting member 130 as illustrated in FIG. 14 comprises a sleeve portion 132 featuring an outer thread 133 engaged with an inner thread 95 of the drive sleeve 90. Moreover, the dose limiting member 130 comprises a proximally extending bracket portion 137 featuring two axially extending and parallely-oriented branches 138, 139 that are mutually interconnected with their proximal ends to form a closed frame structure.

As illustrated for instance in FIG. 15, a proximal end of the bracket portion 137 extends in proximal direction from a proximal end of the drive sleeve 90. By means of the bracket portion 137, the dose limiting member 130 can be rotatably fixed to the housing 20.

For instance, a correspondingly extending pin that may e.g. radially extend from the housing 20 may protrude through the closed frame structure of the bracket portion 137 in radial direction, thereby effectively inhibiting that the dose limiting member 130 rotates as the drive sleeve 90 is set in rotation by means of the drive spindle 80. Due to the threaded engagement of the dose limiting member 130 and the drive sleeve 90 the dose limiting member 130 experiences a proximally-directed displacement relative to the drive sleeve 90 when the drive sleeve 90 is rotated in a dose incrementing direction 5.

Since a direct mechanical interaction or contact between the drive sleeve 90 and the piston rod 120 is not required, the dose limiting member 130 can be arranged inside the drive sleeve 90 in a rather contactless configuration relative to the piston rod 120, which also extends therethrough. Internal friction of the drive mechanism 3 can therefore be reduced.

Moreover and as illustrated in FIG. 14, the piston rod 120 comprises a stop member 124 which is adapted to engage with the dose limiting member 130 when a maximum number of doses has been dispensed by the drive mechanism 3. In the present embodiment, the stop member 124 of the piston rod 120 comprises a radially outwardly extending flange portion to engage with the proximally-located rim 136 of the sleeve portion 132 of the dose limiting member 130. Preferably, the faces of the stop member 124 and the sleeve portion 132 that face towards each other and which get in direct mutual contact when a last dose configuration is reached comprise a geared structure.

Hence, a distally-facing portion of the stop member 124 may comprise a geared flange, e.g. in form of a crown wheel 128. Correspondingly, also the proximal face of the sleeve portion 132 may comprise a geared rim or a crown wheel portion 136 to mate with the crown wheel 128 of the piston rod 120. Such a configuration may be beneficial with such embodiments, where the piston rod 120 rotates when it is driven in distal direction 1 during dose dispensing.

Mutually engaging crown wheels 128, 136 of the piston rod 120 and the dose limiting member 130 may then immediately inhibit any further rotation of the piston rod 120 relative to the rotatably fixed dose limiting member 130. Said mutual engagement is of particular benefit, when the complete content of the cartridge 12 has been expelled. Then, dose limiting member 130 and piston rod 120 are securely interlocked and effectively impede any further incrementing dose setting.

The dose limiting member 130 effectively serves as a last dose limiter. In an initial configuration of the drive mechanism 3 as for instance illustrated in FIG. 15, the dose limiting member 130 will travel in proximal direction 2 during a dose incrementing rotation of drive spindle 80 and drive sleeve 90. Since the dose setting of a single dose is limited by the axially confined displacement of the drive member 70, the dose limiting member 130 will at maximum reach a proximal end position, in which the sleeve portion 132 still remains in the drive sleeve 90.

In such a configuration the dose limiting member 130 will be separated from the stop member 124 of the piston rod 120. During a consecutive dose dispensing action, the piston rod 120 will advance in distal direction 1 relative to the drive sleeve 90. Since a distally-directed dispensing displacement of the piston rod 120 comes along with a dose decrementing rotation of the drive sleeve 90, also the dose limiting member 130 will return into its initial zero dose configuration as for instance illustrated in FIG. 14.

There may be provided a stop member inside the drive sleeve 90 to provide a well-defined distal stop for the dose limiting member 130. However, such a zero dose stop is not necessarily required for the dose limiting member 130 since the dose decrementing rotation 6 of the drive sleeve 90 is already delimited by the drive member 70 engaging with a distal stop 28 of the housing 20.

With a consecutive dose setting procedure, the dose limiting member 130 will repeatedly displace in axial direction 2. Since the piston rod 120 has moved in distal direction 1 during the previous dose dispensing procedure, the stop member 124 of the piston rod 120 continuously approaches to the axial range in which the dose limiting member 130 is displaceable. If the position of the piston rod 120 corresponds to a dose size smaller than the maximum size of a single dose, e.g. smaller than 120 I.U., the stop member 124 of the piston rod 120 may enter the drive sleeve 90 as for instance illustrated in FIG. 14.

In a proceeding dose setting procedure, the dose incrementing rotation of the drive sleeve 90 is immediately stopped, when the proximally-advancing dose limiting member 130 axially engages with the stop member 124 of the piston rod 120. In this way, it can be assured, that the sum of consecutive doses set and dispensed does not exceed the total amount of doses of the medicament contained in the cartridge 12.

The stop member 124 may comprise a lateral recess in order to receive and to pass by the bracket portion 137 of the dose limiting member 130. Additionally or alternatively, it is also conceivable, that the dose limiting member 130 is splined to the piston rod 120 itself. As for instance illustrated in FIG. 4, the dose limiting member 130 may comprise a radially inwardly extending protrusion 135 to engage with an axially extending groove 122 of the piston rod 120. In this way, the dose limiting member 130 can be rotatably locked to the piston rod 120. In such an alternative embodiment, the piston rod 120 should be rotatably fixed to the housing. Here, the piston rod 120 could be splined to the housing 20.

Figure 16:
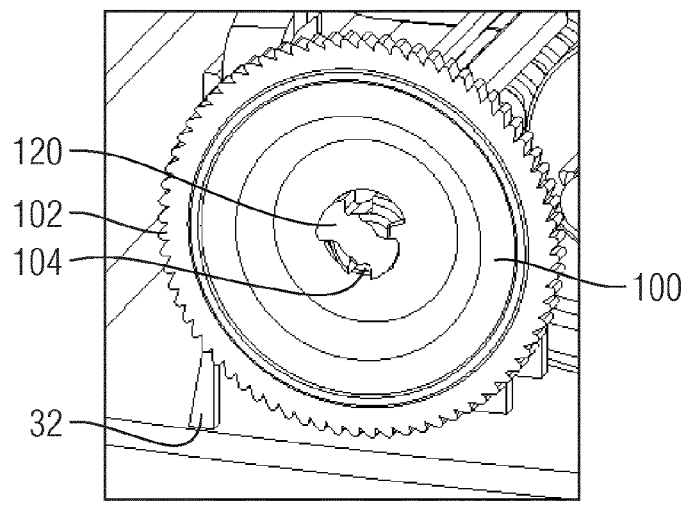
FIG. 16 shows a perspective view of a drive wheel engaged with the piston rod.

In the following dispensing of a dose will be described. For dispensing of a dose the drive sleeve 90 rotates in a dose decrementing direction 6 in such a way, that the torque of the drive sleeve 90 is transferred to a distally-directed displacement of the piston rod 120. As illustrated in FIG. 14, the drive sleeve 90 is coaxially aligned with a drive nut or drive wheel 100. The drive wheel 100 comprises a radially outwardly extending geared rim 102. The teeth of said rim 102 comprise a saw tooth profile and engage with a ratchet member 32 of the housing 20 as illustrated in FIG. 16.

By means of the mutual engagement of the ratchet member 32 with the geared rim 102 rotation of the drive wheel 100 is only allowed in a dose dispensing or dose decrementing direction. A counter-directed movement is effectively blocked and inhibited by said engagement. Moreover, during a dose decrementing or dose dispensing rotation of the drive wheel 100, the ratchet member 32 generates an audible click sound thereby providing an audible feedback to the user, that the injection or dose dispensing is in progress.

The drive wheel 100 further comprises a through opening to receive the piston rod 120 therethrough. The piston rod comprises an outer thread 121 and/or a longitudinally extending groove 122. By means of a groove 122 the piston rod 120 could be rotatably fixed to the housing 20. By means of a threaded engagement of the piston rod 120 with an inner thread 104 of the drive wheel 100, the rotation of the axially fixed drive wheel 100 can be transferred into a distally-directed displacement of the piston rod 120.

In an alternative but not illustrated embodiment, it is also conceivable, that the piston rod 120 is splined to the drive wheel 100 and that the piston rod 120 is threadedly engaged with a housing portion. In such a technically equivalent configuration, rotation of the drive wheel 100 equally transfers into a distally-directed displacement of the piston rod 120 relative to the housing 20 and relative to the barrel of the cartridge 12.

A torque to rotate the drive wheel 100 is provided by the drive sleeve 90, which is axially displaceable between a proximal stop position, in which the drive sleeve 90 is decoupled or disengaged from the drive wheel 100 and hence from the piston rod 120. In its distal stop position, the drive sleeve 90 operably engages with the drive wheel 100 in a torque transmissive way.

As for instance illustrated in FIG. 15, the drive sleeve 90 comprises a radially outwardly extending flange portion 92 at its distal end. From said flange portion 92, there extends a geared rim 93 radially outwardly. The distal end face of the geared rim comprises a ring structure to mate with a correspondingly-shaped flange portion of drive wheel's geared rim 102. Between the rim 102 and the rim 93 there is provided a disc spring 110 which serves to displace the drive sleeve 90 in proximal direction 2.

Hence, drive sleeve 90 and drive wheel 100 can be axially coupled against the action of the disc spring 110 positioned there between. The rim portions 93, 102 of drive sleeve 90 and drive wheel 100 carrying and supporting the disc spring 110 are substantially flat-shaped. In order to transfer angular momentum between the drive sleeve 90 and the drive wheel 100 the drive sleeve 90 comprises a crown wheel portion 94 radially inwardly from the geared rim 93. Correspondingly, the drive wheel 100 comprises a proximally extending socket featuring a correspondingly-shaped crown wheel 106.

When the drive sleeve 90 is displaced in distal direction 1 to get in direct contact with the drive wheel 100, said crown wheels 94, 106 mutually engage and angular momentum acting on the drive sleeve 90 may equally transfer to the drive wheel 100, thereby leading to a distally-directed displacement of the piston rod 120. A distally-directed displacement of the drive sleeve 90 against the action of the disc spring 110 is inducible by a dose dispensing button 40 provided at a proximal end of the housing 20.

Figure 17:
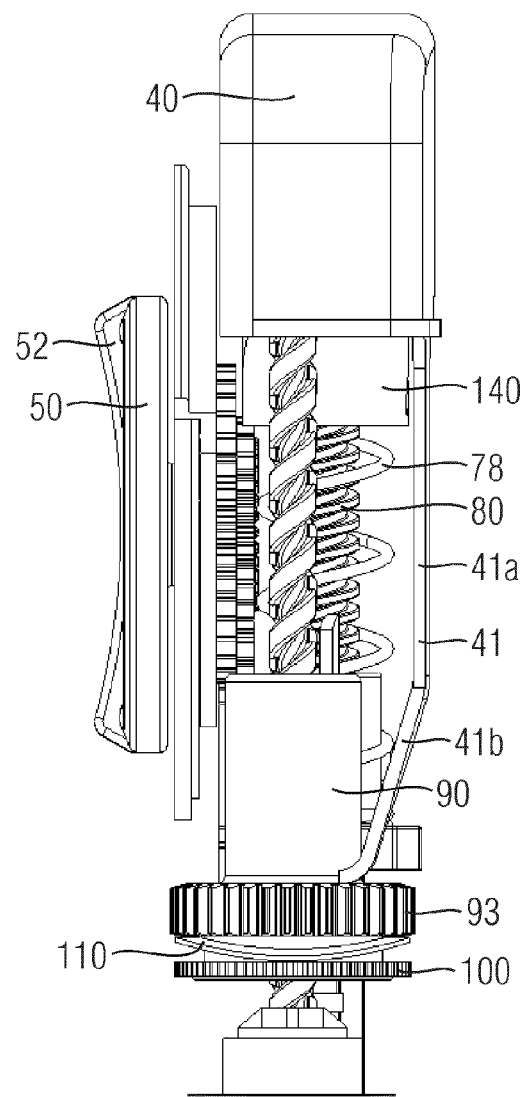
FIG. 17 shows an isolated side view of the drive mechanism without the housing, FIG. 18 schematically shows the mutual interaction of the drive spindle with the drive sleeve.
Figure 18:
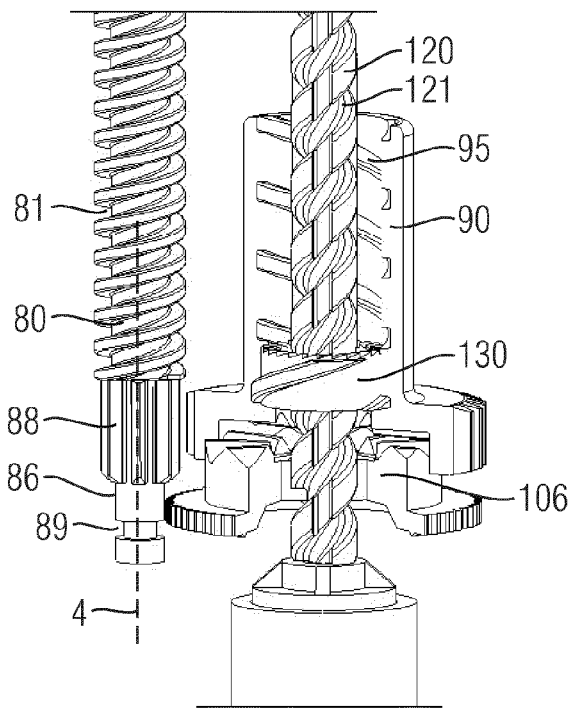
Figure 19:
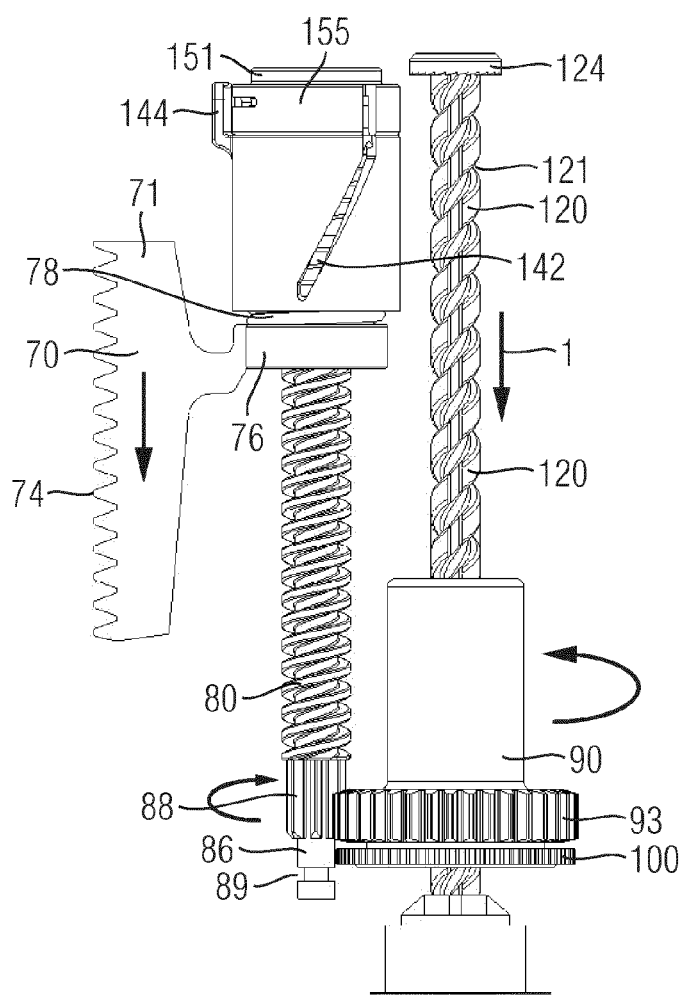
FIG. 19 shows a configuration of the drive mechanism with the drive member in its proximal stop position, FIG. 20 schematically illustrates the assembly of the drive mechanism inside a lower housing portion.

As for instance illustrated in FIG. 17, the dose dispensing button 40 comprises a distally extending strut 41 to but against a proximal-facing portion of the radially outwardly extending flange portion 92 of the drive sleeve 90. The strut 41 comprises a proximal rather axially extending strut portion 41a and a distal strut portion 41b which extends at a predefined angle with respect to the axial direction. In this way, the strut 41 is at least resiliently deformable to a certain degree so that a clutch between the drive sleeve 90 and the drive wheel 100 remains engaged even when the position of the dose dispensing button 40 in axial direction varies to a certain extent.

Depression of the dose dispensing button 40 in distal direction 1 not only engages the drive sleeve 90 and the drive wheel 100. Additionally, distally-directed displacement of the dose dispensing button 40 leads to a release of the drive spindle 80 relative to the ratchet member 150.

Figure 21:
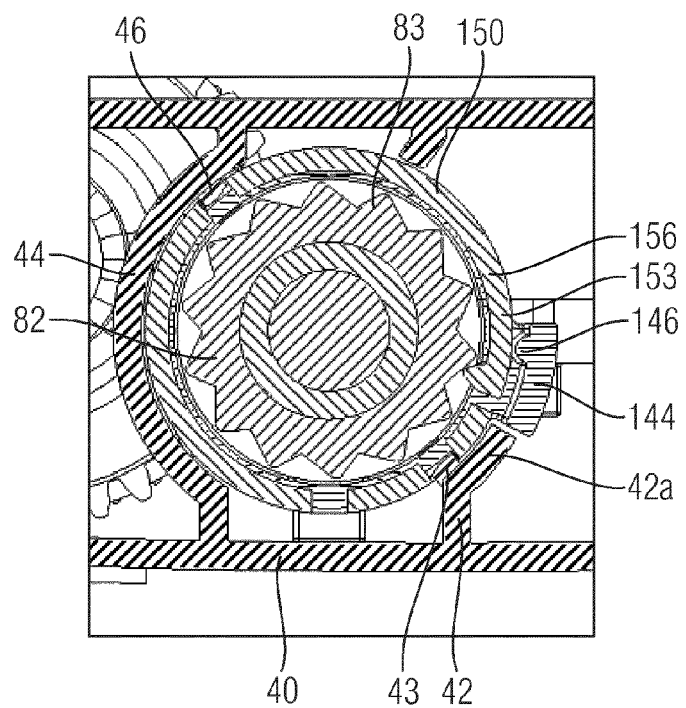
FIG. 21 shows a cross-section along B-B together with the dose dispensing button.
Figure 23:
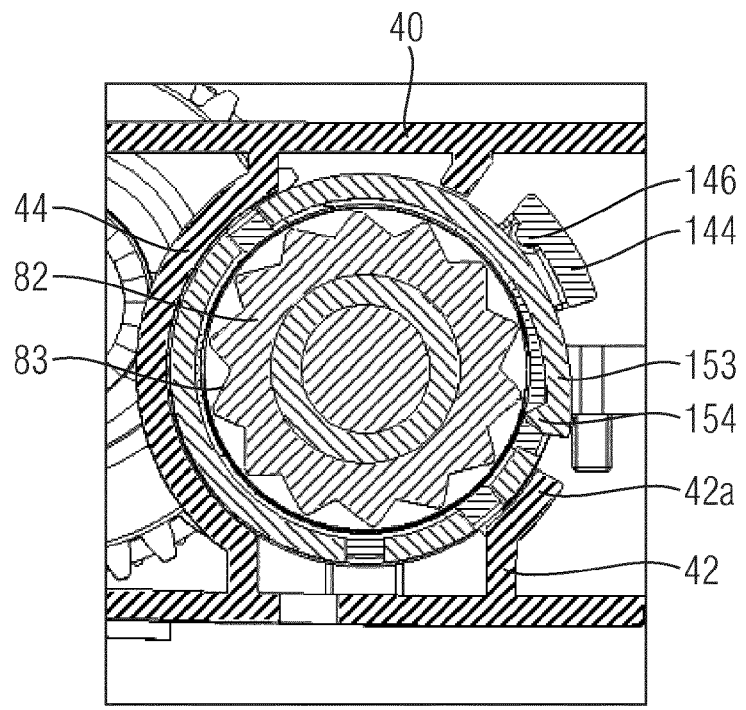
FIG. 23 shows a cross-section B-B according to FIG. 2 with the regulating member in a release configuration.

As becomes apparent from a comparison of FIGS. 21 and 23, the latch element 153 is resiliently deformable in radial direction. As shown in the released configuration according to FIG. 23, the latch element 153 radially protrudes from the outer circumference of the sidewall 156 of the cup-shaped ratchet member 150. In this configuration, the radially inwardly extending lug 154 provided at the free end of the resiliently deformable latch element 153 is no longer engaged with the teeth 83 of the toothed rim 82 of the drive spindle 80.

In the released configuration the drive spindle 80 is effectively free to rotate under the action of the relaxing spring element 78 and the spindle gear of drive spindle 80 and drive member 70 which is driven by said spring element 78.

In the locked or engaged configuration according to FIG. 21, the arc-shaped latch element 153 is biased radially inwardly so that its radially inwardly extending lug 154 engages with the teeth 83 of the drive spindle 80. Radially-directed displacement of the latch element 153 is governed by a biasing member 144 provided at a proximal end of a sleeve-shaped regulating member 140.

Figure 22:
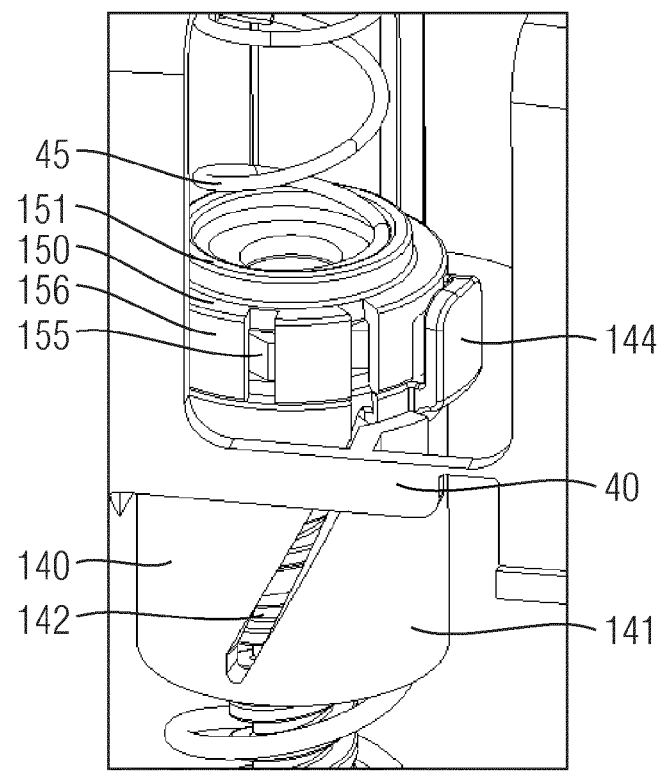
FIG. 22 shows an enlarged perspective view of the mutual engagement of the dose setting button with a regulating member.
Figure 24:
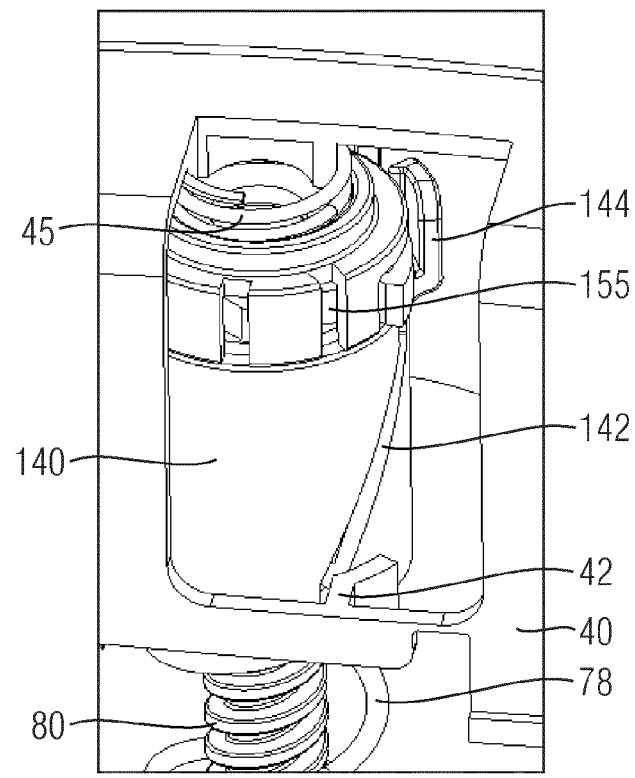
FIG. 24 shows a perspective view according to FIG. 22 with the dose dispensing button fully depressed.

The regulating member 140 is rotatably and coaxially arranged to the ratchet member 150 as for instance illustrated in FIGS. 22 and 24. The regulating member 140 comprises a sleeve portion 141 featuring at least one inclined slit 142 or a respective groove on its outer circumference. As illustrated in FIG. 21 the dose dispensing button 40 comprises an inwardly extending guiding member 42 featuring a radially inwardly extending pin 43 engaging with the inclined slit 142 of the regulating member 140.

Due to the inclined orientation of the slit 142 relative to the axial direction, a distally-directed displacement of the dose dispensing button 40 leads to continuous rotation of the regulating member 140. As a consequence, the biasing member 144 travels along the outer circumference of the arc-shaped latch element 153. Here, the biasing member 144 comprises a radially inwardly extending bulged portion 146 which abuts with an outer circumference of the arc-shaped latch element 153.

In the interlocked configuration, which corresponds to the dose dispensing button 40 in its proximal stop position, the biasing member 144 is fairly close to the free end of the arc-shaped latch element 153. A depression of the dose dispensing button 40 in distal direction 1 comes along with a corresponding rotation of the regulating member 140 and leads to a continuous displacement of the biasing member 144 along the outer circumference of the arc-shaped latch element 153.

As a consequence and as illustrated in FIG. 23, the free end of the latch element 153 may extend radially outwardly. Due to the engagement of the guiding member 42 of the dose dispensing button 40 with the inclined slit 142 of the regulating member 140, the degree of rotation of the regulating member 140 and its biasing member 144 is directly correlated to the degree of axial depression of the dose dispensing button 40.

Due to the resiliently deformable properties of the arc-shaped latch element 153, the holding force provided by the latch element 153 and acting on the toothed rim 82 of the drive spindle 80 can be continuously and steplessly reduced or modified. In this way, mutual friction and gliding behaviour of the latch element 153 and the toothed rim 82 of the drive spindle 80 can be modified in dependence of the depth or degree of axial depression of the dose dispensing button 40.

Depending on the degree of rotation of the regulating member 140, the holding force acting on the drive spindle 80 during an injection procedure can be continuously modified, thereby allowing to regulate the angular velocity of the drive spindle 80 when rotating in a dose decrementing, hence in a dose dispensing orientation 6.

It is to be mentioned here, that the dispensing velocity regulation provided by the mutual interaction of drive spindle 80 and ratchet member 150 can be realized in a variety of different ways. The orientation of the drive spindle 80 serving as a rotatable member and/or the concrete mechanical interaction between the drive spindle 80 and the ratchet member 150 may vary from the illustrated embodiment.

It is only required that the ratchet member 153, generally serving as a clutch member 153, is at least partially radially displaceable with respect to the orientation of the axis of rotation 4 of the drive spindle 80 or of a respective rotatable element 80. Moreover, the mutual retarding interaction of ratchet member 150 and drive spindle 80 can be frictionally based. Additionally, a positive engagement of ratchet member 150 and drive spindle 80 may also exhibit a combined friction-based and positively engaging interaction.

As further illustrated by a comparison of FIGS. 22 and 24, the dose dispensing button 40 is coupled with the proximal end of the ratchet member 150 by means of a spring element 45, e.g. an injection spring 45, typically designed as a compression spring. As further illustrated in FIG. 21 the dose dispensing button 40 is intersected by a strut 44 having a half shell shape which at least partially adopts the outer circumference of the ratchet member 150. In the half shell-shaped portion the strut 44 further comprises an additional pin 46 to engage with a further slit 142 of the regulating member 140.

The regulating member 140 may therefore comprise two oppositely disposed slits 142 to engage with correspondingly arranged radially inwardly extending pins 43, 46 of the dose dispensing button 40. The inwardly extending guiding member 42 of the dose dispensing button 40 further comprises an outer guiding portion 42a, which also adopts the outer shape of the ratchet member 150. By means of the outer guiding portion 42a and the half shell strut 44, the dose dispensing button 40 can be axially guided along the ratchet member 150.

For a secure fastening of the spring element 45, the proximal end of the ratchet member 150 comprises a stepped portion 151 to receive the spring element 45 therein.

As becomes further apparent from FIGS. 21 and 22, the ratchet member 150 comprises axially extended notches 155 that allow to guide the radially inwardly extending pins 43, 46 of the dose dispensing button 40 past the ratchet member 150 during final assembly of the drive mechanism 3.

Depression of the dose dispensing button 40 in distal direction 1 for dispensing of a dose may then be divided into two consecutive steps. In a first step the dose dispensing button 40 is displaced in distal direction by a distance so that the pins 43, 46 advance in distal direction 1 into the slits 142 of the regulating member 140. During this initial displacement the axially extending strut 41 already serves to mutually engage the drive sleeve 90 and the drive wheel 100.

In this way, a torque transmissive coupling of the drive sleeve 90 with the piston rod 120 can be attained even before the drive spindle 80 and hence the drive member 70 are released from the ratchet member 150. It is only due to a further depression of the dose dispensing button 40 in distal direction 1, that the pins 43, 46 run along the slit or groove 142 leading to a releasing rotation of the regulating member 140 and to a gradual and continuous release of the latch element 153. The torque transmissive coupling of drive sleeve 90 and piston rod prior to a release of the drive spindle 80 from the ratchet member can be controlled and governed by the flexural behaviour and by the geometric design of the latch element 153. As already explained above, the depth of depression of the dose dispensing button 40 may determine or may at least influence the angular velocity of the drive spindle 80 during dose dispensing.

Under the action of the relaxing spring element 78, the drive member 70 will return into its initial zero dose configuration. Since the toothed rack portion 71 of the drive member 70 is geared with the sprocket 60 of the gear wheel 58, the dose indicating wheel 54, 56 will count down accordingly. Just before approaching an initial zero dose configuration, the drive member 70 may audibly engage with a clicking member 36 of the housing 20.

Figure 26:
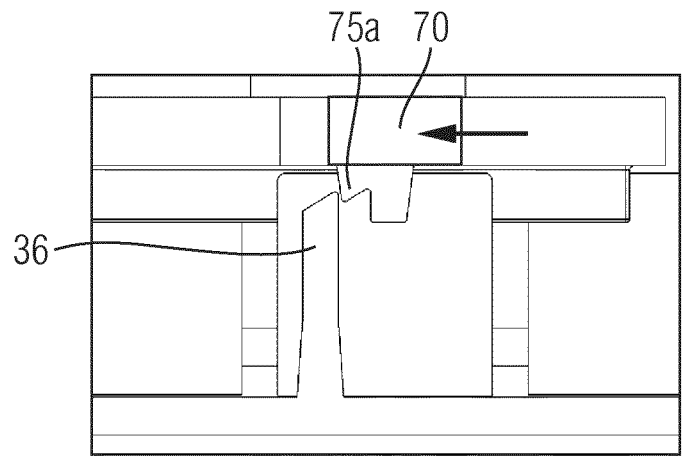
FIG. 26 shows a longitudinal cross-section of the drive member before reaching a zero dose configuration and FIG. 27 is indicative of the drive member reaching the zero dose configuration.
Figure 27:
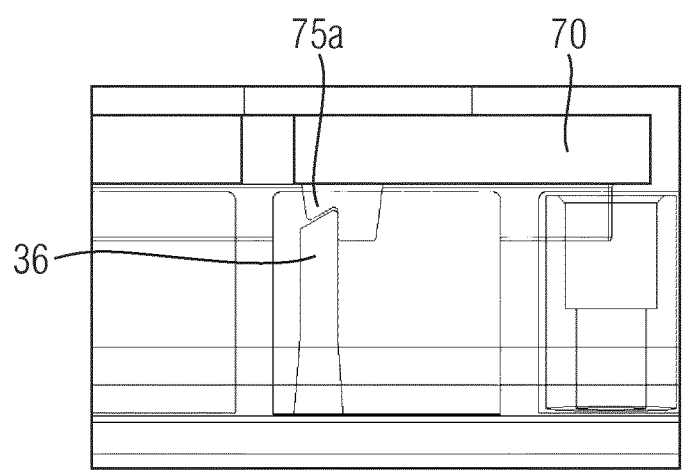

As shown in FIG. 26, the drive member 70 comprises a ledge 75a to engage with an inwardly extending pin-like clicking member 36. Just before reaching a zero dose configuration at the end of a dose dispensing procedure, the bevelled ledge 75a engages with the correspondingly bevelled clicking member 36, thereby generating an audible click sound, in particular when the resiliently deformable clicking member 36 returns into an initial abutment configuration with the bevelled ledge 75a as illustrated in FIG. 27. This audible feedback indicates to the user that a dispensing procedure has terminated.

LIST OF REFERENCE NUMERALS 1 distal direction
2 proximal direction
3 drive mechanism
4 axis of rotation
5 dose incrementing direction
6 dose decrementing direction
10 drug delivery device
12 cartridge
14 piston
15 needle assembly
16 needle hub
17 needle cap
20 housing
21 upper housing portion
22 lower housing portion
23 cartridge window
24 cap
25 socket
26 dose indicating window
27 proximal stop
28 distal stop
29 receptacle
29a slit
30 clicking member
31 clicking member
32 ratchet member
33 bearing
36 clicking member
37 fixing rim
38 guiding structure
40 dose dispensing button
41 strut
41a proximal strut portion
41b distal strut portion
42 guiding member
42a outer guiding portion
43 pin
44 strut
45 spring element
46 pin
50 dose setting member
51 receptacle
52 gripping bar
53 crown wheel
54 dose indicating wheel
55 sprocket
56 dose indicating wheel
57 geared rim
57a crown wheel
58 gear wheel
59 geared rim
60 sprocket
61 ring structure
62 cog
70 drive member
71 toothed rack portion
72 sleeve portion
73 bar
74 tooth
75 ridge portion
75a ledge
76 rim
77 protrusion
78 spring element
79 inner thread
80 drive spindle
81 outer thread
82 toothed rim
83 tooth
86 pinion
88 tooth
89 bearing portion
90 drive sleeve
92 flange portion
93 geared rim
94 crown wheel
95 inner thread
100 drive wheel
102 geared rim
104 inner thread 106 crown wheel
110 disc spring
120 piston rod
121 thread
122 groove
124 stop member
126 pressure piece
128 crown wheel
130 dose limiting member
132 sleeve portion
133 outer thread
135 protrusion
136 geared rim
137 bracket portion
138 branch
139 branch
140 regulating member
141 sleeve portion
142 slit
144 biasing member
146 bulged portion
150 ratchet member
151 stepped portion
153 latch element
154 lug
155 notch
156 sidewall

The invention claimed is:

1. A drug delivery device for setting and dispensing of a dose of a medicament, the device comprises:
an elongated housing;
a cartridge being arranged in the housing, the cartridge containing the medicament and comprising a piston to displace the medicament;
a piston rod configured to be engaged with the piston to displace the piston in a distal direction along a longitudinal axis of the elongate housing;
a drive spindle operably engageable with the piston rod during dose dispensing; and
a drive member comprising a hollow sleeve portion and an axially extending toothed rack portion the hollow sleeve portion being threadedly engaged with the drive spindle, and the drive member being displaceable relative to the drive spindle along the longitudinal axis against a biasing force of a spring element during dose setting and being threadedly engaged with the drive spindle to form a spindle gear,
wherein the drive member is displaceable in a proximal direction along the longitudinal axis against the biasing force of the spring element for setting the dose during the dose setting, and
wherein the drive member is displaceable in the distal direction under the biasing force of the spring element for dispensing the dose during the dose dispensing, displacement of the drive member in the distal direction being configured to rotate the drive spindle in dose decrementing direction during the dose dispensing.

2. The drug delivery device according to claim 1, further comprising a dose setting member rotatable mounted to a sidewall of the housing.

3. The drug delivery device according to claim 2, wherein the rack portion of the drive member is engaged with a pinion of a gear wheel operably engaged with the dose setting member.

4. A drive mechanism of a drug delivery device for setting and dispensing of a dose of a medicament, the drive mechanism comprising:
an elongated housing;
a piston rod configured to be engaged with a piston of a cartridge to displace the piston in a distal direction along a longitudinal axis of the housing;
a drive spindle operably engageable with the piston rod during dose dispensing; and
a drive member comprising a hollow sleeve portion and an axially extending toothed rack portion, the hollow sleeve portion being threadely engaged with the drive spindle, and the drive member being displaceable relative to the drive spindle along the longitudinal axis against a biasing force of a spring element during dose setting and being threadedly engaged with the drive spindle to form a spindle gear,
wherein the drive member is displaceable in a proximal direction along the longitudinal axis against the biasing force of the spring element for setting the dose during the dose setting, and
wherein the drive member is displaceable in the distal direction under the biasing force of the spring element for dispensing the dose during the dose dispensing, displacement of the drive member in the distal direction being configured to rotate the drive spindle in a dose decrementing direction during the dose dispensing.

5. The drive mechanism according to claim 4, further comprising a dose setting member rotatably mounted to a sidewall of the housing.

6. The drive mechanism according to claim 5, wherein the dose setting member is rotatably engaged with a first dose indicating wheel and with a second dose indicating wheel to display at least first and second digits, respectively, of a number in a dose indicating window of the housing.

7. The drive mechanism according to claim 5, wherein the rack portion of the drive member is engaged with a pinion of a gear wheel operably engaged with the dose setting member.

8. The drive mechanism according to claim 1, wherein the drive member is axially slidably disposed in the housing.

9. The drive mechanism according to claim 1, wherein the drive member is axially displaceable relative to the housing between a distal stop and a proximal stop.

10. The drive mechanism according to claim 1, wherein the spring element comprises a compression spring extending around the drive spindle.

11. The drive mechanism according to claim 1, wherein the spring element axially extends between the drive member and the drive spindle.

12. The drive mechanism according to claim 1, wherein the drive spindle comprises a toothed rim rotatably engaged with a ratchet member.

13. The drive mechanism according to claim 12, wherein the ratchet member comprises an arc-shaped latch element variably stressable in a radial direction such that the latch element is selectively engageable and disengageable with the toothed rim of the drive spindle.

14. The drive mechanism according to claim 12, further comprising a pinion fixed to a distal end of the drive spindle and geared with a drive sleeve rotatably supported in the housing.

15. The drive mechanism according to claim 14, wherein the drive sleeve is axially displaceable between a distal stop position and a proximal stop position, the drive sleeve being configured to be rotatably engaged with the piston rod in the distal stop position and to be rotatably disengaged from the piston rod in the proximal stop position.

16. The drive mechanism according to claim 14, further comprising a dose dispensing button displaceable along the longitudinal axis and being located at a proximal end of the housing, the button being configured to engage with the ratchet member in a dose setting mode and with the drive sleeve in a dose dispensing mode.

17. A drive mechanism of a drug delivery device for setting and dispensing of a dose of a medicament, the drive mechanism comprising:
- an elongated housing;
- a piston rod configured to be engaged with a piston of a cartridge to displace the piston in a distal direction along a longitudinal axis of the housing;
- a drive spindle comprising a toothed rim rotatably engaged with a ratchet member and operably engageable with the piston rod during dose dispensing;
- a pinion fixed to a distal end of the drive spindle and geared with a drive sleeve rotatably supported in the housing;
- a dose dispensing button displaceable along the longitudinal axis and being located at a proximal end of the housing, the button being configured to engage with the ratchet member in a dose setting mode and with the drive sleeve in a dose dispensing mode; and
- a drive member displaceable relative to the drive spindle along the longitudinal axis against a biasing force of a spring element during dose setting and being threadedly engaged with the drive spindle to form a spindle gear.

18. The drive mechanism according to claim 17, farther comprising a dose setting member rotatably mounted to a sidewall of the housing.

19. The drive mechanism according to claim 18, wherein the dose setting member is rotatably engaged with a first dose indicating wheel and with a second dose indicating wheel to display at least first and second digits, respectively, of a number in a dose indicating window of the housing.

20. The drive mechanism according to claim 17, wherein the drive member is axially slidably disposed in the housing.

* * * * *

UNITED STATES PATENT AND TRADEMARK OFFICE
CERTIFICATE OF CORRECTION

PATENT NO. : 10,149,947 B2  
APPLICATION NO. : 14/782705  
DATED : December 11, 2018  
INVENTOR(S) : Stefan Bayer et al.

Page 1 of 1

It is certified that error appears in the above-identified patent and that said Letters Patent is hereby corrected as shown below:

In the Claims

Column 25, Line 41, Claim 1, delete "portion" and insert -- portion, --

Column 25, Line 59, Claim 2, delete "rotatable" and insert -- rotatably --

Column 26, Line 9, Claim 4, delete "threadely" and insert -- threadedly --

Column 26, Line 12, Claim 4, delete "clement" and insert -- element --

Column 26, Line 37, Claim 8, delete "claim 1," and insert -- claim 4, --

Column 26, Line 39, Claim 9, delete "claim 1," and insert -- claim 4, --

Column 26, Line 42, Claim 10, delete "claim 1," and insert -- claim 4, --

Column 26, Line 45, Claim 11, delete "claim 1," and insert -- claim 4, --

Column 26, Line 48, Claim 12, delete "claim 1," and insert -- claim 4, --

Column 28, Line 9, Claim 18, delete "farther" and insert -- further --

Signed and Sealed this  
Sixteenth Day of July, 2019

Andrei Iancu  
*Director of the United States Patent and Trademark Office*